(12) United States Patent
Ahnsorge et al.

(10) Patent No.: US 7,524,833 B2
(45) Date of Patent: *Apr. 28, 2009

(54) METHOD AND APPARATUS FOR CONCENTRATING AND STABILIZING CONJUGATED ESTROGENS FROM MARE URINE

(75) Inventors: Juergen Ahnsorge, Neustadt am Ruebengerge (DE); Ivan Ban, Hannover (DE); Heinz-Helmer Rasche, Burgdorf (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 147 days.

This patent is subject to a terminal disclaimer.

(21) Appl. No.: 11/451,472

(22) Filed: Jun. 13, 2006

(65) Prior Publication Data

US 2006/0234994 A1    Oct. 19, 2006

Related U.S. Application Data

(60) Division of application No. 10/112,040, filed on Apr. 1, 2002, now Pat. No. 7,081,451, which is a continuation of application No. PCT/EP01/08657, filed on Jul. 26, 2001.

(30) Foreign Application Priority Data

Aug. 1, 2000  (DE) ............................... 100 37 389

(51) Int. Cl.
*A61K 31/56*    (2006.01)
(52) U.S. Cl. ..................................... 514/170
(58) Field of Classification Search ................ 514/170
See application file for complete search history.

(56) References Cited

U.S. PATENT DOCUMENTS

| 2,519,743 | A | 8/1950 | Cruise |
| 2,834,712 | A | 5/1958 | Beall et al. |
| 3,769,401 | A | 10/1973 | Thompson et al. |
| 5,723,454 | A | 3/1998 | Ban et al. |
| 5,814,624 | A | 9/1998 | Ban et al. |

FOREIGN PATENT DOCUMENTS

| DE | 2 150 819 | | 4/1972 |
| GB | 821989 | | 10/1959 |
| GB | 2230856 | * | 10/1990 |
| WO | WO 98/08525 A1 | | 3/1998 |
| WO | WO 98/08526 A1 | | 3/1998 |

OTHER PUBLICATIONS

Shackleton et al., Clinica Chimica Acta, vol. 107, pages.*
Heikkinen et al., "Reversed-Phase $C_{18}$ Cartridge for Extraction from Urine and Plasma," *Clin. Chem.*, 1981, vol. 27, No. 7, pp. 1186-1189.
Shacketon et al., "Use of Sep-pak® Cartridges for Urinary Steroid Extraction: Evaluation of the Method for Use Prior to Gas Chromatographic Analysis," *Clinica Chimica Acta*, 1980, pp. 231-243, vol. 107.
Bradlow et al., "Extraction of Steroid Conjugates with a Neutral Resin," *Steroids*, 1968, pp. 265-272, vol. 11.

* cited by examiner

*Primary Examiner*—Barbara P Badio
(74) *Attorney, Agent, or Firm*—Crowell & Moring LLP

(57) ABSTRACT

A method and apparatus for concentrating and stabilizing conjugated estrogens from pregnant mare urine on solid adsorbent supports to obtain a starting material for pharmaceuticals that contain a natural mixture of conjugated estrogen mixtures on cartridges in the vicinity of the horses. The adsorbent cartridges can be loaded at the site of urine collection so it is unnecessary to transport large volumes of urine to a central processing point. The loading process can take continuously over a period of weeks until the column is saturated. The effluent urine remains at the site where facilities for its disposal are available. Only the loaded cartridge is transported, and transport can occur at longer intervals of up to several weeks. The stability of the conjugated estrogens on the adsorber assures there is no risk of decomposition.

43 Claims, 2 Drawing Sheets

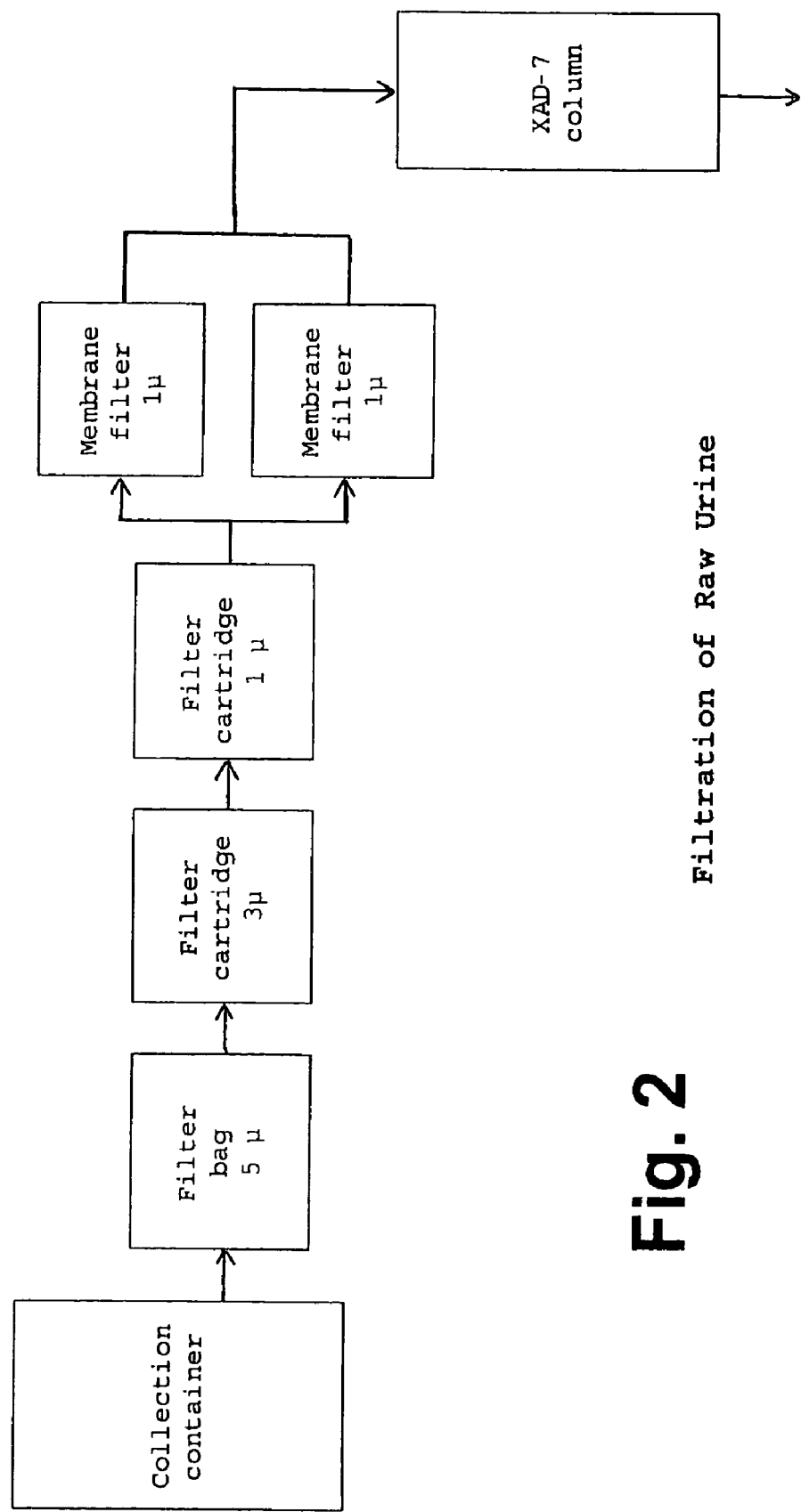
Fig. 2   Filtration of Raw Urine

METHOD AND APPARATUS FOR CONCENTRATING AND STABILIZING CONJUGATED ESTROGENS FROM MARE URINE

CROSS REFERENCE TO RELATED APPLICATIONS

This application is a divisional of U.S. patent application Ser. No. 10/112,040, filed Apr. 1, 2002, now U.S. Pat. No. 7,081,451, which is a continuation of International patent application Serial No. PCT/EP01/08657, filed Jul. 26, 2001 which claims priority to Germany patent application No. 100 37 3889.5, the entire disclosures of which are hereby incorporated in their entireties.

BACKGROUND OF THE INVENTION

The present invention relates to a method and an apparatus for concentrating and stabilizing conjugated estrogens from pregnant mare urine onto solid supports in order to obtain a suitable starting material for producing pharmaceuticals that contain the natural mixture of these conjugated estrogens as the active component.

Estrogens are used in the medical field for hormone substitution therapy. In particular, estrogen mixtures are used for the treatment and prophylaxis of change-of-life conditions in women after natural or artificial menopause. In this regard, natural mixtures of conjugated estrogens present in pregnant mares' urine are particularly effective and well tolerated.

The dissolved solid content in pregnant mares' urine (hereinafter abbreviated as "PMU") can naturally fluctuate in a wide range, generally 40-90 g total solids per liter. In addition to urea and other typical components of urine, phenolic substituents in quantities of approximately 2-5 wt-% relative to total solids are contained in PMU solids. These phenolic substituents include cresols and dihydro-3,4-bis[3-hydroxyphenol)methyl]-2 (3H)-furanone, known as HPMF. These substances may be present in the free or conjugated form. PMU contains a natural mixture of estrogens which are very prevalent in the conjugated form, as the sulfuric acid hemiester sodium salt, for example, (hereinafter abbreviated as "sulfate salt"). The content of conjugated estrogens (hereinafter abbreviated as "CE") can be calculated as estrogen sulfate salt, and ranges between 0.3 and 1 wt-%, relative to total solids.

Various methods have been described in the prior art for the direct preparation and recovery of conjugated estrogens contained in PMU. Extracts containing conjugated estrogens are usually obtained from PMU by extraction with a polar organic solvent immiscible or sparingly miscible in water, such as acetic acid ethyl ester, n-butanol, or cyclohexanol, for example. However, numerous problems arise in such liquid-liquid extractions, such as intense foam formation, sedimentation, emulsification, and strong phase separation. Several extraction steps are generally required, which results in losses and only partial recovery of the estrogen. To avoid these disadvantages, therefore, a number of solid phase extraction methods have been proposed in the prior art.

In order to obtain small quantities of urine and plasma liquids for analytical determination of estrogens by gas chromatography, Heikkinnen et al. (Clin. Chem. 27/7, (1981), 1186-1189) and Shackleton et al. (Clinica Chimica Acta 107 (1980) 231-243) have described solid phase extraction of estrogens using a cartridge comprising silanized silica gel containing octadecylsilane groups (Sep-Pak® $C^{18}$ cartridge, manufactured by Waters Ass. Inc., Milford, Mass., USA). In this method the estrogens were eluted from the cartridge with methanol.

In 1968, H. L. Bradlow (see Steroids 11 (1968), 265-272) proposed the use of Amberlite XAD-2™, a neutral, nonpolar hydrophobic polystyrene resin from Rohm and Haas for the extraction of conjugated estrogens. The stated adsorption capacity is low. According to Bradlow, optionally diluted urine was conducted at a low throughput rate through a column containing the resin. The estrogens were eluted with methanol or ethanol.

Recent patent applications describe methods for obtaining an extract containing a natural mixture of conjugated estrogens from mare urine by solid phase extraction of the mixture of conjugated estrogens from pregnant mare urine on, for example, RP silica gel (International Patent WO 98/08525) or on nonionized, semipolar polymeric adsorbent resins (International Patent WO 98/08526).

In addition to the aforementioned optimization of the direct, complete preparation of pregnant mare urine (PMU) for obtaining natural mixtures of CE, steps preceding the preparation, such as securing protective storage for the estrogens and handling the collected urine at the collection site, are of particular importance for the yield and quality of the estrogen-containing raw materials and of the natural mixture of conjugated estrogens isolated therefrom. In this regard, measures to optimize the transport of the collected estrogen-containing raw materials from the collection site to the site of actual preparation and isolation of conjugated estrogens are also desirable.

The complete processing of PMU, for example by solid phase extraction, requires qualified personnel trained in chemical and pharmacological methods in order to observe under well-controlled conditions the exacting requirements for purity and quality of a substance or substance mixture used as a pharmaceutical agent. Collection of the urine (PMU), however, usually takes place in the normal environment of the pregnant mares, that is, at stud farms in rural and often remote locations. As a rule, only a simple infrastructure is present here, and the collection and handling of urine (PMU) is typically carried out by ordinary personnel following instructions, so that high standards for handling the collected urine cannot be expected.

However, conjugated estrogens in the composition excreted in pregnant mare urine are a complex mixture containing in particular sodium estrone sulfate, sodium equilin sulfate, and other CE. It is very important in the isolation of CE that the PMU be processed as quickly as possible in fresh condition. Under extended storage urine rapidly begins to decompose, turning a dark color and giving off the odor of ammonia, with the CE content declining drastically. The rate of decomposition is a function of the storage conditions and the purity criteria. For this reason, the collected urine (PMU), which involves large volumes of liquid, hitherto has had to be transported daily from the collection site to a centralized processing point to assure the most rapid processing possible.

Hence, there is a pressing need for suitable methods and apparatus for concentrating and stabilizing conjugated estrogens contained in pregnant mare urine directly at the collection site, in a manner that is most protective of the product and allows the greatest ease in handling, and for the most efficient transport from the collection site to the site of processing and isolation.

SUMMARY OF THE INVENTION

The object of the present invention, therefore, is to develop a suitable technical method for the recovery of a natural mixture of conjugated estrogens and a suitable device for concentrating and stabilizing conjugated estrogens (CE) from the collected urine of pregnant mares (PMU), while avoiding the aforementioned disadvantages.

In particular, it is an object that the method and the device allow conjugated estrogens from PMU to be concentrated and stabilized at the site where the urine is collected, in a manner that protects the product and allows ease in handling, and allow the most efficient transport of the estrogen-containing raw material thus prepared, from the collection site to the site of actual preparation and isolation of the natural mixture of conjugated estrogens.

Surprisingly, it has been found that conjugated estrogens bound to solid adsorbent supports are very stable and durable in storage over long periods of time, with no signs of decomposition.

The present invention, therefore, relates to a method for concentrating and stabilizing mixtures of conjugated estrogens from pregnant mare urine in a manner that meets requirements in the field and is decentralized, that is, particularly close to the stable or pasture, characterized in that the natural mixture of conjugated estrogens contained in pregnant mare urine is concentrated and stabilized on a solid adsorbent support, and that a predetermined maximum total amount of collected, optionally previously strained liquid urine is pumped from a supply vessel, continuously or in discrete portions, at a predetermined flow rate through an upright cartridge, and the liquid urine runoff is discarded, whereby the cartridge is packed with a suitable adsorbent, which is (continuously) surrounded by liquid, for the adsorption of a predetermined quantity of the mixture of conjugated estrogens contained in the liquid urine, with the maximum total amount of liquid urine pumped through the cartridge, which is predetermined as the end point check for the loading of the adsorbent, being matched to the maximum loading capacity of the adsorbent for the conjugated estrogens contained in the liquid urine.

In the context of the invention, the phrase "meets requirements in the field" means that the method is adapted at the site to the requirements of the collection practice, and is therefore simple and safe to manage by trained personnel; that is, it is uncomplicated and capable of being carried out with the substantial exclusion of possible operator error.

As used herein, the term "decentralized" means that the method can be carried out at a particular site of the urine collection operation without specialized chemical or pharmaceutical apparatus, that is, particularly close to the stable and/or pasture.

The term "cartridge" as used here means any type of closed column having a closeable inlet and outlet, in addition to connection elements such as quick couplings. Thus, within the scope of the present invention the term "cartridge" also encompasses columns as they are customarily used in laboratories, pilot plants, and the chemical industry, for example, and which are equipped to be used according to the invention as discussed above.

According to the inventive method, a raw or starting material is prepared which serves for the advantageous production of pharmaceuticals containing the natural mixture of conjugated estrogens from PMU as an active component, in which the natural estrogen mixture content of the PMU is essentially completely concentrated on the adsorbent (support) and can be stabilized over a rather long period under the normal environmental conditions of the particular collection site. After complete (maximum) loading, the cartridge can be easily exchanged and replaced with a cartridge containing an unloaded adsorbent.

The cartridges with loaded adsorbents may be stored at the site for quite a long time at ambient temperature or optionally under refrigeration down to approximately 4° C., and, for specific requirements, also frozen down to approximately −20° C., for example, until a certain number of loaded cartridges is present for practical transport to the centralized processing point. The transport may take place at ambient temperatures or, for storage as described above, under cooling or refrigeration.

The actual processing and isolation of the natural mixture of conjugated estrogens (CE) can then occur in a conventional manner in the centralized processing point for the particular adsorbent, for example, by washing and elution of CE from the adsorbent and further processing of the eluate by customary means. For example, the eluate may be further concentrated in a generally known manner to obtain a concentrate which is substantially or completely free of organic solvent and suitable for further pharmaceutical processing.

If desired, a solids mixture that is free of elution agents may be prepared by other suitable drying methods such as spray drying, fluidized bed drying, freeze drying, or vacuum drying. The eluate containing the estrogen mixture as well as a concentrate prepared therefrom or a spray-dried solid product may be incorporated by customary methods into solid or liquid pharmaceutical preparations such as tablets, dragées, capsules, or emulsions.

In addition to the inventive method, the invention also relates to an apparatus that can be used in the method of the invention, taking into account in a useful manner the requirement for simplicity at the site of use and assuring that the method is carried out in a manner that is safe and protective of the product. This apparatus according to the invention is suitable for concentration and stabilization in a manner that meets requirements in the field and is decentralized, that is, particularly close to the stable or pasture.

The following description contains a general discussion of several additional process parameters that are important in carrying out the method. With regard to specialized construction or apparative designs of suitable devices for carrying out the method according to the invention, reference is made to the following detailed description of the apparatus of the invention, which may be used to supplement the general description of the procedural method given below.

In the method according to the invention, the collected PMU may be used as such, and to this end the daily collected quantity of PMU is first stored in a supply vessel. As an option, it is recommended that coarse mechanical contaminants such as straw, hay, or the like be removed beforehand, for example by using a simple wide-mesh screen while filling the supply vessel with the freshly collected PMU. If desired, preservatives, germicides, bactericides, and/or anthelmintic agents may be added to the collected urine in the supply vessel to reduce the bacterial and viral counts.

The PMU is regularly pumped from the supply vessel to the adsorbent-containing cartridge once or twice a day, for example, depending on the amount of urine present, using a pump such as a hose pump. This cartridge typically has dimensions and weight which permit manual handling by a person of average strength. With regard to the method, it is recommended that the internal dimensions of the cartridge be designed for the receiving adsorption bed, such that the cartridge can accommodate approximately 30 to 50 liters of adsorbent, and the PMU is preferably required to travel a path distance of preferably 80 to 120 cm from the cartridge inlet to the outlet. According to the invention, the conjugated estrogens are adsorbed onto the adsorbent by contact of PMU with the adsorbent, whereby the liquid urine is conducted, at either the head or base end, into an upright cartridge containing the adsorbent, and during throughput is maintained in contact with the adsorbent for a sufficient time for the estrogen to be adsorbed, until the leftover urine finally exits the opposite end of the cartridge. The PMU is conducted through the cartridge at the head or base end, for example, to assure that the adsorbent is continuously surrounded by liquid in order to eliminate to the extent possible undesired dry operation of the cartridge.

The contact time and the flow rate are matched to the particular adsorbent, and for adsorbents suitable for the method (loading velocity) should be in the range of 3 to 10 adsorber bed volumes/hr, preferably 4 to 6 adsorber bed volumes/hr. For example, particularly suitable loaded flow velocities lie in the range from 4.5 to 5.5 adsorber bed volumes/hr. Particular contact times and flow rates for especially preferred adsorbents are described in further detail below.

The maximum total quantity of liquid urine that can be conducted through the cartridge is a function of the adsorption capacity of the particular adsorbent, and for adsorbents suitable for the method should be in the range of 20 to 60 adsorber bed volumes, preferably 30 to 40 adsorber bed volumes. The maximum total quantity of liquid urine that can be led through the cartridge for loading, depending on the adsorbent and the size of the cartridge, generally is in the range of 900 to 2,000 liters. The particular end value of the throughput quantity is strictly specified for the operator at the collection site. Thus, a simple flow meter, such as a water meter, may be used to measure the quantity of liquid urine pumped through the cartridge. After the maximum loading is reached, the operation is optionally switched to a parallel, second cartridge and the adsorption process is continued on this cartridge.

When the predetermined end value for the cartridge is reached, the cartridge with the adsorbed CE may be washed if desired with water, for example, and/or another suitable aqueous wash solution, before the liquid feed is interrupted. The liquid outlet and the liquid inlet are then closed and the connection, such as a simple quick coupling, at the liquid inlet to the cartridge is detached. The loaded cartridge can then be removed and stored at a suitable location until being transported to the centralized processing point, and a new, unloaded cartridge can be attached to the liquid inlet.

After loading with PMU, for example before replacing a cartridge which is completely loaded with PMU or before reaching the total loading capacity subsequent to any individual partial loading steps, the cartridge may be rinsed, if desired, with water and/or another suitable aqueous wash solution such as a basic wash solution, especially diluted aqueous sodium hydroxide, for example (such as aqueous 0.5-2N NaOH) to remove leftover liquid urine from the cartridge. The quantity of wash solution is not critical, and is preferably chosen to be sufficient to expel leftover urine from the cartridge without also washing out appreciable quantities of conjugated estrogens. It has proven useful to use, for example, one to three, preferably approximately two, bed volumes of wash liquid per bed volume of adsorbent. In this regard, it is useful to conduct the wash water or wash liquid through the cartridge containing the adsorbent at a flow rate of 3 to 10, preferably 5 to 7 parts by volume wash water per 1 part by volume adsorbent per hour. The adsorbent loaded with CE in the cartridge may serve as the raw or starting material for the isolation of pure CE for the production of pharmaceuticals containing the natural mixture of conjugated estrogens.

In a variant of the invention, after washing with water and/or wash solution, to further stabilize the adsorbed CE the cartridge may undergo a final rinse with a preservative solution, such as a solution containing a preservative agent, a pH-adjusted aqueous solution, and/or an aqueous salt solution, before detaching the cartridge from the device and replacing it with a new cartridge. To prevent bacterial contamination of the column, particularly during storage or transport without refrigeration, customary preservatives and also germicides, bactericides, and/or anthelmintic agents, for example, may be used. A pH adjustment of the wash water depends on the particular adsorbent used. Aqueous solutions of inorganic salts in different concentrations may be used as salt solutions, for which examples are given in Table III.1. The use of salt solutions is particularly recommended when the cartridges loaded with CE are to be stored under cooling or in particular, under refrigeration. Preferred salt solutions are sodium chloride solutions having salt concentrations of approximately 10 to 35 wt-%, preferably 25 to 33 wt-%.

In a preferred embodiment of the method according to the invention, the collected urine is preferably freed of viscous and fine-particle solids before being pumped from the supply vessel to the cartridge. It is therefore useful to first conduct the liquid urine from the supply vessel through one or more prefilters before pumping the liquid urine through the cartridge. In this manner, the PMU can be passed through at least one conventional separation device, for example, a filtration system having at least one deep-bed filter or precoated filter. As a separation device, a deep-bed filter having a sand bed, for example, or a commercially available filter cartridge may be used, or also commercially available precoated filters or plate filters, cartridge filters, filter bags, or filtration tubes. The filters may be used individually or in any desired combination with one another, for example, connected successively in series or in parallel.

If desired, filtering aids may be added to the liquid urine (PMU) before filtration. Suitable filtering aids include those which bind calcium carbonate and/or mucin, thereby improving the urine filtration. The filter may also be optionally connected to a downstream particle separator. For example, in the case of a sand bed, the filter may be connected to a downstream sand separator.

The principles and techniques of filtration are known to those skilled in the art. With regard to the object to be achieved by the invention, the conventional principles of clarification come into consideration. The object of clarification is to purify the liquid phase so that the purity of the filtrate is the significant parameter for achieving the process goal. The separation process is basically implemented by the interaction between the filter material and the suspension. This is important in the selection of the filter material for the process modeling as well as for the process control design of the filter apparatus.

In most cases, the separated solid exerts a controlling influence on the course of the process. Thus, with a sufficient portion of solids and in view of the potential of the solids to form bridges in which particles are supported over the filter material without plugging the filter, the filter cake which forms and continuously grows assumes the function of the filter material. In this case for coated filtration and cake filtration, the structure of the filter cake determines the course of the process, whereas the actual filter material after an initial phase has only a supporting function.

The site of the solids separation is a further significant feature for differentiating filtration processes. In surface filtration, the solids on the surface of the filter material are separated by a sieve effect, that is, as the result of the size ratio of the solid particles to the pores of the filter material. In contrast, in deep-bed filtration, the solid particles penetrate into the filter material and settle in the interior of the material.

The adsorbent, with which the cartridge may be filled, can generally be any inorganic or organic adsorbent that has sufficient adsorption capacity for the natural mixture of conjugated estrogens contained in the PMU. Suitable adsorbents for use in the cartridge thus include polymeric adsorber resins, silica gel, RP silica gel, and/or preferably semipolar polymeric adsorber resins.

The hydrophobized silica gels which may be used as adsorbents in the cartridge include, for example, generally known reverse phase silica gels (abbreviated as "RP silica gels"), which are chemically modified silica gels bearing hydrophobic functional groups or ligands. Silanized RP silica gels which contain n-octadecyldimethylsilyloxy, n-octyldimethylsilyloxy, or dimethylhydroxysilyloxy groups as hydrophobic functional groups, for example, are suitable. Silanized silica gels having average particle sizes of, for example, 15 to 500 μm are suitable. Silica gels containing dimethylhydroxysilyloxy groups having an average particle size ranging from 0.05 to 0.3 mm, such as silica gel 60/dimethylsilane derivative from Merck, have proven to be particularly useful.

It is advantageous to conduct the liquid urine through the silica gel-containing cartridge at a throughput rate such that the contact time is sufficient for adsorption of the estrogen. Throughput rates corresponding to a throughput of 5 to 20 parts by volume PMU per 1 part by volume silica gel/hour are suitable. The adsorption is preferably carried out at room temperature. It can be useful to control the throughput rate of liquid urine through the reactor by operating at a slight positive pressure (controlled by the power of the pump).

The quantity of hydrophobized silica gel to be used may vary, depending on the type of silica gel used and the solids content in the collected liquid urine. By using PMU which has been prefiltered (i.e., freed of viscous and solid materials), one part by volume hydrophobized silica gel, for example, can be loaded with up to eighty parts by volume pretreated PMU without noticeable quantities of estrogen being detectable in the liquid urine effluent.

The semipolar polymeric adsorbent resins which may be used in the cartridge as adsorbents are preferably porous organic nonionic polymers which, in contrast to nonpolar hydrophobic polymeric adsorbent resins, have an intermediate polarity (for example, having a dipole moment of the active resin surface in a range of 1.0 to 3.0, particularly 1.5 to 2.0, Debye) and a slightly hydrophilic structure, for example, polycarboxylic acid ester resins. It is advantageous to use macroporous semipolar resins having a preferably macroreticular structure and average pore diameters ranging from 50 to 150, preferably 70 to 100 Å, and a specific surface ranging from 300 to 900, preferably 400 to 500 $m^2/g$. Macroporous crosslinked aliphatic polycarboxylic acid ester resins, especially crosslinked polyacrylic ester resins such as Amberlite XAD-7® from Rohm and Haas, have proven to be particularly suitable.

It is useful to conduct the liquid urine through the cartridge containing the adsorbent resin with a throughput rate such that the contact time is sufficient for adsorption of the estrogen. Suitable throughput rates correspond, for example, to a throughput of 3 to 10, preferably 5 to 7 parts by volume PMU per 1 part by volume adsorber resin/hour. The adsorption is preferably carried out at room temperature. The throughput rate of liquid urine through the reactor may be advantageously controlled by operating at a slight positive pressure (controlled by the power of the pump). The quantity of semipolar adsorber resin to be used can vary depending on the type of adsorber resin employed and the solids content in the collected liquid urine. By use of PMU, one part by volume adsorber resin, such as crosslinked aliphatic polycarboxylic acid ester adsorber resin, for example, may be loaded with up to eighty parts by volume pretreated PMU without noticeable quantities of estrogen being detectable in the liquid urine effluent.

In addition to the aforementioned preferred adsorbents, other types of adsorber resins or silica gels may also be used. In this regard, nonpolar, semipolar, and even polar adsorber resins are suitable adsorber resins. The quantity of resin that can be pumped through the adsorbent is determined beforehand, based on the particular adsorbent capacity. Examples of adsorber resins which may be used include commercially available types such as polymeric Amberlite adsorbents having a styrene divinylbenzene backbone chain (for example, XAD-1180, XAD-2, XAD-4, XAD-16), an acrylic ester backbone chain (for example, XAD-7), or highly polar backbone chains containing nitrogen and oxygen (for example, XAD-12). Other adsorber resins are Dowex resin (copolymers of styrene and divinylbenzene), such as Dowex 112, Dowex Optipore, Dowex Optipore V 493; Lewatits (crosslinked polystyrenes) such as Lewatit OC 1064, Lewatit OC 1066, or Lewatit OC 1163; and polyamine anion exchange resins such as Dowex resins. Adsorber resins XAD-7, XAD-16 (HP type), XAD 118, and Dowex Optipore, preferably Dowex Optipore V 493, and Lewatits OC 1064, OC 1066, and OC 1163 are particularly advantageous.

In addition to the aforementioned inventive method, the invention further relates to an apparatus which may be used in the method of the invention, and which effectively takes into account the simple conditions at the site of use and assures that the method may be carried out in a safe manner that protects the product.

The apparatus according to the invention is characterized by its suitability for concentrating and stabilizing mixtures of conjugated estrogens (CE) contained in pregnant mare urine (PMU) onto a solid support (adsorbent) in a manner that meets requirements in the field and is decentralized, that is, located near the stable or pasture. The apparatus comprises:

an upright cartridge packed with a suitable adsorbent, which is (continuously) surrounded by liquid, for the adsorption of a predetermined quantity of the mixture of conjugated estrogens contained in the liquid urine of pregnant mares, with the cartridge having either a) a liquid inlet situated at the base end and a liquid outlet situated at the head end or b) a liquid inlet situated at the head end and a liquid outlet situated at the base end, and a pump, a flow meter, and a throughput meter arranged in the stated sequence upstream of the cartridge and connected to one another by hose lines.

The apparatus according to the invention is intended to carry out the aforementioned method for concentrating and stabilizing conjugated estrogens (CE) contained in PMU in a manner that meets requirements in the field and is decentralized. If desired, the device may also contain two cartridges connected in parallel which may be operated concurrently or alternately.

The cartridge used in the apparatus according to the invention may be designed in a broad dimensional range with regard to its height and diameter. However, in order not to impair handling in the field, the size and weight of the cartridge should be designed so that it is easily handled and carried by hand, for example, during replacement of loaded cartridges with new, unloaded cartridges, by a person of average strength. For example, the cartridge should be designed so that the internal dimensions of the adsorption bed can accommodate 30 to 50 liters of adsorbent, and the internal height in particular is in the 80 to 120 cm range. The inner diameter of the cartridge generally ranges from 10 to 25 cm. Those skilled in the art are able to design precise dimensions of the cartridge to assure optimal flow conditions during operation.

Furthermore, the cartridge used in the apparatus according to the invention preferably is made of robust, durable, and chemically resistant materials as customarily used in the production of devices for the chemical industry, such as impact-resistant laboratory glass, plastic, and/or metal such as sheet steel.

Any pump with a simple and robust construction may be used in the device according to the invention, such as a monopump, hose pump, or membrane pump. For example, a hose pump has proven to be a useful pump for the apparatus of the invention.

Any flow meter with a simple and robust construction may be used in the device according to the invention, such as a rotameter, vane air flow meter, or inductive flow meter. For example, a rotameter with a float has proven to be a useful flow meter for the apparatus of the invention.

Any throughput meter with a simple and robust construction may be used in the device according to the invention to measure the quantity of liquid urine pumped through the cartridge, such as a water meter or inductive flow meter. A water meter, for example, has proven to be a useful flow meter for the apparatus of the invention.

In one useful variant of the apparatus according to the invention, at least one or more prefilters, such as deep-bed filters or precoated filters, are connected in-line between the pump and the flow meter. The filter may be a deep-bed filter having a sand bed or a commercially available filter cartridge or a commercially available precoated filter, plate filter, cartridge filter, filter bag, or filtration tube. In addition, a particle separator may optionally be connected downstream of the prefilter, such as the example of a sand separator connected downstream of a sand bed being used as a prefilter.

In variants of the invention, the filters may be used singly or in any desired combination with one another, such as connection in series and/or in parallel. An advantageous embodiment of these variants is characterized in that the prefilter is a module composed of two prefilters connected in parallel which are individually operated in alternation, and which may be replaced by new prefilters when the device is running.

A further advantageous embodiment of this variant is characterized in that the filter system comprises a module composed of a prefiltration unit, connected in series, made of prefilters (filter bags, for example) in addition to one or two deep-bed filters and two absolute filters (membrane filters, for example) connected thereto in parallel, the absolute filters being individually operated in alternation, and which also may be replaced by new filters when the device is running. Furthermore, to check proper functioning of the prefilter it may be useful in the device according to the invention to connect an in-line manometer between the pump and the prefilter and an in-line manometer in the region downstream of the prefilter, preferably just behind the flow meter.

BRIEF DESCRIPTION OF THE DRAWINGS

The invention will be described in further detail hereinafter with reference to illustrative preferred embodiments depicted in the accompanying drawings, in which:

FIG. 2 is a block diagram illustrating the method and apparatus of the invention.

DETAILED DESCRIPTION OF PREFERRED EMBODIMENTS

Figure 1:
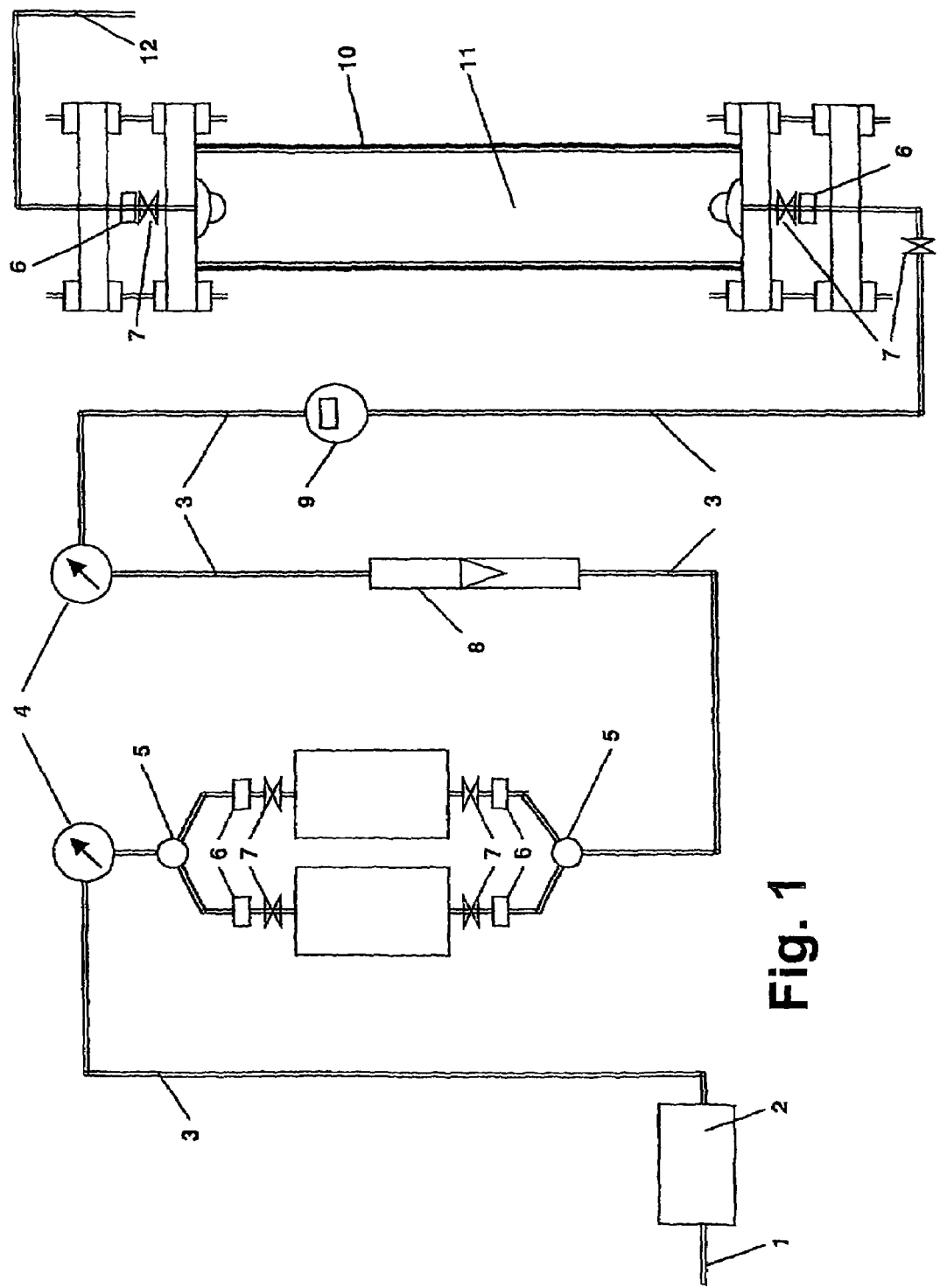
FIG. 1 is a schematic illustration one possible embodiment of an apparatus according to the invention for carrying out the method of the invention.

As noted, FIG. 1 shows a schematic apparatus for stabilizing and concentrating conjugated estrogens from pregnant mare urine according to a preferred embodiment of the invention. FIG. 2 is a schematic representation of the method for a variant of filtering raw urine.

The method according to the invention and the apparatus according to the invention have a number of advantages, of which the most important will be briefly stated below. Concentration of conjugaated estrogens, that is, loading of the adsorption columns, may be carried out directly at the collection site, thereby eliminating the daily transport of large quantities of liquid urine to a centralized processing point. Loading may be performed continuously over a rather long time, up to several weeks, until the adsorption column is saturated. For example, using adsorber resin XAD-7, the quantity of adsorbed urine is approximately thirty-five bed volumes.

The leftover urine freed of conjugated estrogens remains at the site, where suitable devices for disposal are already available. The loaded column, that is, only about $1/35$ of the original weight of the liquid urine, is transported. Transport may take place at rather long time intervals and may take longer, for example, up to a few weeks. The excellent stability of the CE on the adsorption column ensures that there is no risk of decomposition. There is no treatment of large quantities of urine in a separator and an ultrafiltration facility, since any viscous substances and sediment present are separated from the initially collected urine by using robust and maintenance-free precoated filters or deep-bed filters (for example, sand filters, filter cartridges, precoated filters, plate filters, cartridge filters, filter bags, or filtration tubes) which, if necessary, may be easily replaced.

FIG. 1 schematically illustrates an advantageous device for stabilizing and concentrating conjugated estrogens from pregnant mare urine. The elements of the apparatus identified by reference numerals have the following meanings: (1) inlet for the liquid urine from the supply vessel, (2) pump, such as a hose pump, (3) connecting lines, (4) manometers, (5) three-way line, (6) quick couplings, (7) closure valves, (8) filter, (9) flow meter with float (rotameter), (10) throughput meter, such as a water meter, (11) cartridge or column, (12) adsorber bed, (13) outlet.

FIG. 2 is a schematic representation of a method for filtering raw urine, with the filter system comprising a module composed of a prefiltration unit made of prefilters (filter bags, for example) in addition to one or two deep-bed filters and two absolute filters (membrane filters, for example) connected thereto in parallel.

The invention is further illustrated by the following non-limiting examples:

EXAMPLE 1

General Operating Specification for Concentrating and Stabilizing Conjugated Estrogens Contained in Pregnant Mare Urine Directly at the PMU Collection Site by Adsorption onto an Adsorbent Contained in a Cartridge The collected PMU is filled into a supply vessel via a funnel fitted with a sieve. The sieve has a large mesh aperture and serves the sole purpose of separating coarse mechanical contaminants such as straw, hay, or the like.

The method is explained below by example, using an adsorption column (as a cartridge) containing a semipolar adsorber resin. If cartridges containing other adsorbents are used, the handling and especially the processing of the loaded cartridge may depend on the particular type of adsorbent. The loading process and final washing of the cartridge at the urine collection site were kept essentially as described under A) and B) or, optionally, minimally adapted to any special conditions at the site or to the particular adsorbent.

A) Adsorption of Estrogen in PMU onto an Adsorbent

The adsorption of CE contained in PMU was carried out in an adsorption unit, as shown by example in the sketch in FIG. 1. A predetermined total quantity of PMU, relative to the capacity of the cartridge or the adsorption column, was pumped in whole or in part at ambient temperature and at a predetermined throughput rate through a column or cartridge packed with an adsorbent, after optionally straining and filtering beforehand. As the adsorber, for example, a semipolar polyacrylic ester adsorber resin (Amberlite XAD-7 from Rohm and Haas, particle size 0.3 to 1.2 mm, dipole moment 1.8 Debye, average pore diameter 80 Å, specific surface approximately 450 m$^2$/g, dry) swollen in water, or other suitable adsorbents were used. After reaching the predetermined maximum loading quantity of PMU, the PMU feed to the column or cartridge was stopped and optionally pumped from the loaded column or cartridge to a free column or cartridge connected in parallel. The estrogen in the PMU was completely adsorbed on the adsorption column thus loaded.

B) Washing of the Loaded Adsorption Column

After the adsorption process had ended, the loaded adsorption column or cartridge was facultatively washed with water or another aqueous wash solution such as a basic wash solution, particularly diluted sodium hydroxide solution (0.5-2 N NaOH, for example). To this end, the wash water or wash solution was likewise pumped through the column or cartridge at a predetermined throughput rate of, for example, approximately 5.5 bed volumes per hour. The discharged wash water was discarded.

C) Storage and Transport

For transport or intermediate storage of the loaded adsorption column or cartridge, after conclusion of the adsorption process or after facultative washing (for example, with water or another aqueous, optionally basic wash solution, particularly sodium hydroxide solution, 0.5-2 N NaOH, for example), the column or cartridge was closed off at both ends, removed from loading apparatus, and stored in a suitable location. Storage may occur at ambient temperatures, such as 15 to 30° C., in a standard storage room, or in a refrigerator at temperatures down to approximately 4° C. If the liquid in the adsorption column is protected from freezing, refrigeration can be carried out at lower temperatures, for example, at deep cooling temperatures ranging to approximately −20° C. The loaded columns or cartridges were transported from the collection and storage site, in regular intervals of several days to a few weeks, to a centralized processing point for chemical processing and isolation of the conjugated estrogens by trained personnel.

D) Desorption of Conjugated Estrogens from the Adsorption Column or Cartridge

The loaded columns or cartridges were processed in a customary manner for separation of accompanying substances and isolation of conjugated estrogens appropriate for the particular adsorbent. The processing can take place as described in International Patent Application WO 98/08526 by use of a semipolar adsorber resin of Amberlite such as XAD-7. To this end, the elution liquid was conducted at a suitable flow rate through the column or cartridge preheated to 45° C. The discharged eluate was collected in fractions. The first fraction was approximately 1 bed volume, while the remaining fractions were each approximately 0.75 bed volume. The individual fractions were analyzed by HPLC for estrone sulfate salt, cresol, and HPMF content. The first fraction was collected as long as the eluate was colorless to pale yellow. This fraction consistently contained only traces of estrogen sulfate salt.

After the first bed volume of eluate had been discharged, the eluate turned an intense dark brown color. Approximately 80 to 90% of the total amount of conjugated estrogens adsorbed on the column was consistently contained in the subsequent 2 to 4 fractions. The remaining fractions contained only slight amounts of estrogen sulfate salt. This was also clearly evident by the decrease in color intensity. After distilling off the solvent, the residual fractions may optionally be further processed and additional conjugated estrogens isolated.

The main fractions containing the conjugated estrogens each had a high total solids (TS) content, determined by HPLC, of estrone sulfate salt, and were sufficiently freed of cresol and HPMF so that these fractions, as is, represented suitable extracts for further pharmaceutical processing.

E) Regeneration of the Adsorber Resin Column

The loaded columns or cartridges were regenerated in a customary manner appropriate for the particular adsorbent. The regeneration can take place as described in International Patent Application WO 98/08526 by use of a semipolar adsorber resin of Amberlite such as XAD-7. For the regeneration, the column or cartridge was first washed, for example with an ethanol/water mixture containing 50 wt-% ethanol adjusted to pH 12, then with a 10 wt-% aqueous sodium citrate solution, once again with the ethanol/water mixture, and finally with distilled water. For the adsorber resin referenced as an example, the entire regeneration was carried out at a temperature of 45° C., whereby here as well the regeneration and wash solutions were passed through the column or cartridge at either the base end or the head end. The column or cartridge can be loaded and regenerated multiple times, up to 40 times, for example.

EXAMPLE 2

Stability Tests with Loaded Adsorption Columns for the Determination of Desorbed Conjugated Estrogens Stability tests were performed with adsorption columns loaded with initially collected urine to examine the column stability, that is, the stability of the adsorbed conjugated estrogens. The adsorption columns were loaded in a customary manner, then the adsorber resin was taken from the columns and stored at two temperatures for different periods of time. At the end of the storage time, the adsorbate was eluted and analyzed for conjugated estrogens and accompanying substances. The results were compared to the elution results from control samples, that is, samples that had not been stored.

A) Test Procedure

The absorption was carried out in a 3 liter column packed in a known manner, using semipolar adsorber resin of type Amberlite XAD-7 (semipolar polyacrylic ester resin, that is, Amberlite XAD-7 from Rohm and Haas, having a particle size 0.3 to 1.2 mm, a dipole moment of 1.8 Debye, an average pore diameter of 80 Å, and a specific surface of approximately 450 $m^2/g$, dry). To this end, a quantity of 90 liters (30 bed volumes) of previously ultrafiltered mare urine from Poland was charged on the column at room temperature and a throughput rate of five bed volumes per hour. The estrogen in the pregnant mare urine was completely adsorbed on the semipolar adsorber resin column loaded in this manner. After the column was loaded with the mare urine, the column was subsequently washed with 3 liters of water, and the loaded resin was discharged from the column and divided into 10 samples of 300 ml each. These samples were transferred to smaller columns. One sample was discarded.

The following procedures were then carried out:

1. Immediate elution of the control sample, that is, without storage.
2. Storage of each of the remaining samples at 4° C. or at 25° C.
3. Elution of samples 1 (4° C.) and 2 (25° C.) after one week of storage.
4. Elution of samples 3 (4° C.) and 4 (25° C.) after two weeks of storage.
5. Elution of samples 5 (4° C.) and 6 (25° C.) after five weeks of storage.
6. Elution of samples 7 (4° C.) and 8 (25° C.) after eight weeks of storage.

The elution was carried out in a known manner by first washing the loaded adsorber resin with an aqueous sodium hydroxide solution. After each washing step, the respective wash liquid was analyzed for estrone (as the sulfate salt), equilin, cresol, and HPMF content, using HPLC.

An ethanol/water mixture (30 wt-%, pH 12) made alkaline by the addition of sodium hydroxide was used as the elution liquid, and the resin was eluted at an elution temperature of 45° C. The eluate was collected in fractions, and the individual fractions were analyzed for estrone, cresol, and HPMF content, again using HPLC. The first fraction was collected as long as the eluate was colorless to pale yellow. This fraction contained only traces of estrone (estrogen sulfate salt). After the first bed volume of eluate had been discharged, the eluate turned an intense dark brown color. Approximately 80 to 90% of the total amount of conjugated estrogens adsorbed on the column was consistently contained in the subsequent 2 to 4 fractions. The remaining fractions for regenerating the resin (each at 45° C. in the referenced sequence, with 50 wt-% ethanol at pH 12, 10 wt-% sodium citrate, and water) contained only slight amounts of estrogen sulfate salt. This was also clearly evident by the decrease in color intensity.

B) Results

The results of the column stability tests are presented for individual samples in Tables I.0 through I.9 and summarized in Table I.10, and are discussed in more detail below.

The loading of the column or cartridge with urine (see Table I.0) and elution of the control column (see Table I.1) showed a normal course of adsorption and desorption. However, elevated values of cresol and HPMF were found in the eluate, which could be attributed largely to incomplete laminar flow in the column or to the very high cresol levels (almost 1000 mg/liter) in the initially collected urine.

Tables I.2 through I.9 give the results of elution after storage periods of one, two, five, and eight weeks. The basic objective was to determine that, as a rule, the adsorbed hormones (conjugated estrogens) were quantitatively desorbed. Occasionally, particularly after only one week storage at 25° C., for example, quantitative desorption was determined only during regeneration with 50% ethanol. However, this involved only desorption of conjugated estrogen residues, and the majority had already been isolated in the actual desorption. There appeared to be little or no dependency of desorption on the storage time and temperature, provided, for example, that possible non-optimal flow conditions did not play a greater role in the small columns. However, in all cases the eluate was essentially free of cresol and HPMF. To obtain optimal results, therefore, attention should be directed to optimal column throughput, regardless of the storage time. The columns or cartridges should therefore always be immersed in liquid; that is, dry operation should be avoided.

The results after five weeks' storage presented in Tables I.6 and I.7 show a satisfactory course of elution at a temperature of 4° C., whereas at T=25° C., hormone still appears in the regenerate. The HPMF and cresol content in the eluate was very small in both cases.

Surprisingly, excellent results were obtained even after a very long storage time, as shown in Tables I.8 and I.9 for the eight-week storage. The elution peaks for estrone and equilin were very steep and sharp; that is, the volume of conjugated estrogen eluate was small. The cresol and HPMF values were practically nil.

Table I.10 gives an overview summary of all the tests. The sum of, for example, the estrone content of the eluate and regenerate was within approximately 1055 mg±4% in all cases, in keeping with the expected mass balance.

In summary, it may be concluded that the one- to eight-week storage of the loaded XAD-7 resin at temperatures of 4° C. and 25° C. shows differences in elution behavior and the height and width of the hormone peaks, but not in the sum of all hormones eluted, which taken together were in the range of 1055 mg±4%, relative to the estrone content. It thus follows that the observed qualitative differences are based for the most part only on nonhomogeneous flow conditions in the relatively small columns used, and may be easily avoided by the use of columns or cartridges with dimensions meeting standards in the field.

TABLE I.0

Column test for stability of column material
Loading of column with native urine from Poland, ultrafiltered
Adsorber: XAD-7, volume: 3 liters
After charging on the column, resin was discharged and subsequently
washed with 3 liters of water. The resin was divided into equal portions of
300 ml each and subjected to a column stability test. One resin parcel was
eluted immediately, while the others were stored at room temperature and
under refrigeration.

| a) Samples | Volume liters | Estrone mg/l | HPMF mg/l | Cresol mg/l | Equilin mg/l |
|---|---|---|---|---|---|
| Starting solution (after ultrafiltration) | | | | | |
| Control solution 1 | 30 | 85.4 | 67.2 | 908.0 | 50.1 |
| Control solution 2 | 30 | 117.7 | 96.9 | 990.4 | 70.0 |
| Control solution 3 | 30 | 137.6 | 105 | 997.5 | 80.2 |
|  | 90 = 30 BV | 113.567 = Average | 89.7 | 965.3 | 66.8 |

| b) Samples | Vol. liters | Time hr | Flow l/hr | Flow BV/hr | Estrone mg/l | Equilin mg/l | HPMF mg/L | HPMF mg | Cresol mg/l | Cresol mg |
|---|---|---|---|---|---|---|---|---|---|---|
| Run 1 | 10 | 0.7 | 15 | 5.0 | 0.0 | 0.0 | 142.6 | 1426.0 | 2.7 | 27.0 |
| Run 2 | 10 | 0.7 | 15 | 5.0 | 0.0 | 0.0 | 0.0 | 0.0 | 2.2 | 22.0 |
| Run 3 | 10 | 0.7 | 15 | 5.0 | 0.0 | 0.0 | 0.0 | 0.0 | 0.8 | 8.0 |
| Run 4 | 10 | 0.7 | 15 | 5.0 | 0.0 | 0.0 | 148.5 | 1485.0 | 1.4 | 14.0 |
| Run 5 | 10 | 0.7 | 15 | 5.0 | 0.0 | 0.0 | 150.6 | 1506.0 | 5.2 | 52.0 |
| Run 6 | 10 | 0.7 | 15 | 5.0 | 0.0 | 0.0 | 153.7 | 1537.0 | 27.3 | 273.0 |
| Run 7 | 10 | 0.7 | 15 | 5.0 | 0.0 | 0.0 | 153.8 | 1538.0 | 81.9 | 819.0 |
| Run 8 | 10 | 0.7 | 15 | 5.0 | 0.0 | 0.0 | 155.7 | 1557.0 | 322.4 | 3224.0 |
| Run 9 | 10 | 0.7 | 15 | 5.0 | 0.0 | 0.0 | 154.2 | 1542.0 | 770.5 | 7705.0 |

TABLE I.1

Column test for stability of column material
Elution without storage
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) | | | | | | | | | | | | | | |
| Starting content: | 7700 | | | | | | 113.6 | 874.7 | 89.7 | 690.7 | 965.3 | 7432.8 | 66.8 | 514.4 |
| Washing: water with NaOH (2%), pH 13 | | | | | | | | | | | | | | |
| Wash 1 | 300 | 12 | 25 | 5.0 | 9.4 | | 102.6 | 30.8 | 37.2 | 11.2 | 1423.1 | 426.9 | 53.6 | 16.1 |
| Wash 2 | 300 | 12 | 25 | 5.0 | 13.1 | | 29.5 | 8.9 | 216.0 | 64.8 | 5000 | 1500.0 | 48.4 | 14.6 |
| Wash 3 | 300 | 12 | 25 | 5.0 | 13.1 | | 12.8 | 3.8 | 110.8 | 33.2 | 5000 | 1500.0 | 30.5 | 9.2 |
| Wash 4 | 300 | 12 | 25 | 5.0 | 13.2 | | 99.8 | 2.9 | 45.7 | 13.7 | 2000 | 600.0 | 9.8 | 2.9 |
| Wash 5 | 300 | 12 | 25 | 5.0 | 13.2 | | 8.4 | 2.5 | 54.1 | 16.2 | 1023.3 | 307.0 | 5.0 | 1.5 |
| Elution: Ethanol 30%, 45° C., pH 12 | | | | | | | | | | | | | | |
| Eluate 1 | 300 | 12 | 25 | 5.0 | 13.1 | 3.6 | 109.2 | 32.8 | 585.1 | 175.5 | 565.8 | 169.7 | 56.3 | 16.9 |
| Eluate 2 | 300 | 12 | 25 | 5.0 | 13.0 | 1.9 | 2099.2 | 629.8 | 0.0 | 0.0 | 394.8 | 118.4 | 1209.8 | 362.9 |
| Eluate 3 | 300 | 12 | 25 | 5.0 | 12.7 | 0.6 | 815.6 | 244.7 | 1.0 | 0.3 | 119.9 | 36.0 | 466.9 | 140.1 |
| Eluate 4 | 300 | 12 | 25 | 5.0 | 12.5 | 0.2 | 268.8 | 80.6 | 0.0 | 0.0 | 50.8 | 15.2 | 150.2 | 45.1 |
| Eluate 5 | 300 | 12 | 25 | 5.0 | 12.3 | 0.1 | 87.2 | 26.2 | 0.0 | 0.0 | 21.6 | 6.5 | 44.8 | 13.4 |
| Regeneration: 50% ethanol, 45° C., pH 12 | | | | | | | | | | | | | | |
| Regen 1 | 600 | 24 | 25.0 | 5.0 | 12.2 | | 39.1 | 23.5 | 0.0 | 0.0 | 12.0 | 7.2 | 18.8 | 11.3 |
| Regeneration: 10% Na citrate/water, both at 45° C. | | | | | | | | | | | | | | |
| Regen 2 | 600 | 24 | 25 | | 11.7 | | 2.9 | | 0.0 | | 5.9 | | 1.1 | |
| Regen 3 | 600 | 24 | 25 | | 11.3 | | 1.4 | | 0.0 | | 3.8 | | 0.0 | |

TABLE I.2

Column test for stability of column material
Elution after 7 days storage at 4° C.
Adsorber: XAD-7, volume: 300 ml
Starting solution: native urine from Poland, ultrafiltered

| Samples | Vol. ML | Time | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting content: | 7700 | | | | | | 113.6 | 874.7 | 89.7 | 690.7 | 965.3 | 7432.8 | 66.8 | 514.4 |
| *Washing: water with NaOH (2%), pH 13* ||||||||||||||| 
| Wash 1 | 300 | 12 | 25 | 5.0 | 9.5 | | 89.6 | 26.9 | 88.6 | 26.6 | 2604.6 | 781.4 | 42.2 | 12.7 |
| Wash 2 | 300 | 12 | 25 | 5.0 | 13.1 | | 33.7 | 10.1 | 343.7 | 103.1 | 5396.9 | 1619.1 | 58.3 | 17.5 |
| Wash 3 | 300 | 12 | 25 | 5.0 | 13.1 | | 9.0 | 2.7 | 32.4 | 9.7 | 1343.0 | 402.9 | 4.7 | 1.4 |
| Wash 4 | 300 | 12 | 25 | 5.0 | 13.1 | | 9.1 | 2.7 | 0.0 | 0.0 | 611.3 | 183.4 | 4.7 | 1.4 |
| Wash 5 | 300 | 12 | 25 | 5.0 | 13.1 | | 9.3 | 2.8 | 4.3 | 1.3 | 184.0 | 55.2 | 4.6 | 1.4 |
| *Elution: Ethanol 30%, 45° C., pH 12* |||||||||||||||
| Eluate 1 | 300 | 12 | 25 | 5.0 | 13.1 | 3.4 | 174.2 | 52.3 | 4.8 | 1.4 | 129.0 | 38.7 | 92.1 | 27.6 |
| Eluate 2 | 300 | 12 | 25 | 5.0 | 13.0 | 1.7 | 1362.7 | 408.8 | 0.0 | 0.0 | 167.2 | 50.2 | 801.0 | 240.3 |
| Eluate 3 | 300 | 12 | 25 | 5.0 | 12.6 | 0.6 | 887.8 | 266.3 | 0.0 | 0.0 | 99.5 | 29.9 | 512.8 | 153.8 |
| Eluate 4 | 300 | 12 | 25 | 5.0 | 12.4 | 0.4 | 433.6 | 130.1 | 0.0 | 0.0 | 52.9 | 15.9 | 250.0 | 75.0 |
| Eluate 5 | 300 | 12 | 25 | 5.0 | 12.4 | 0.2 | 231.0 | 69.3 | 0.0 | 0.0 | 30.7 | 9.2 | 133.4 | 40.0 |
| *Regeneration: 50% ethanol, 45° C., pH 12* |||||||||||||||
| Regen 1 | 600 | 24 | 25.0 | 5.0 | 12.4 | | 171.6 | 103.0 | 0.0 | 0.0 | 27.8 | 16.7 | 96.1 | 57.7 |
| *Regeneration: 10% Na citrate/water, both at 45° C.* |||||||||||||||
| Regen 2 | 600 | 24 | 25 | | 12.1 | | 18.8 | 11.3 | 0.0 | 0.0 | 0.0 | 0.0 | 0.0 | 0.0 |
| Regen 3 | 600 | 24 | 25 | | 11.2 | | 0.0 | 0.0 | 0.0 | 0.0 | 0.0 | 0.0 | 0.0 | 0.0 |

[see source document for table values; commas in numerical values denote decimal points.]

TABLE I.3

Column test for stability of column material
Elution after 7 days storage, 25° C.
Adsorber: XAD-7, volume: 300 L
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting content: | 7700 | | | | | | 113.6 | 874.7 | 89.7 | 690.7 | 965.3 | 7432.8 | 66.8 | 514.4 |
| *Washing: water with NaOH (2%), pH 13* |||||||||||||||
| Wash 1 | 300 | 12 | 25 | 5.0 | 10.0 | | 98.7 | 29.6 | 168.7 | 50.6 | 4051.7 | 1215.5 | 66.0 | 19.8 |
| Wash 2 | 300 | 12 | 25 | 5.0 | 13.0 | | 26.1 | 7.8 | 208.3 | 62.5 | 4701.1 | 1410.3 | 48.4 | 14.5 |
| Wash 3 | 300 | 12 | 25 | 5.0 | 13.1 | | 8.0 | 2.4 | 55.0 | 16.5 | 3122.5 | 936.8 | 6.6 | 2.0 |
| Wash 4 | 300 | 12 | 25 | 5.0 | 13.1 | | 8.3 | 2.5 | 30.6 | 9.2 | 1710.5 | 513.2 | 5.0 | 1.5 |
| Wash 5 | 300 | 12 | 25 | 5.0 | 13.3 | | 8.7 | 2.6 | 15.1 | 4.5 | 652.9 | 195.9 | 5.8 | 1.7 |
| *Elution: Ethanol 30%, 45° C., pH 12* |||||||||||||||
| Eluate 1 | 300 | 12 | 25 | 5.0 | 13.1 | 3.4 | 182.6 | 54.8 | 11.2 | 3.4 | 323.0 | 96.9 | 96.1 | 28.8 |
| Eluate 2 | 300 | 12 | 25 | 5.0 | 13.0 | 1.7 | 904.3 | 271.3 | 0.0 | 0.0 | 216.5 | 65.0 | 521.3 | 156.4 |
| Eluate 3 | 300 | 12 | 25 | 5.0 | 12.8 | 0.8 | 949.0 | 284.7 | 0.0 | 0.0 | 138.6 | 41.6 | 552.1 | 165.6 |
| Eluate 4 | 300 | 12 | 25 | 5.0 | 12.5 | 0.5 | 611.1 | 183.3 | 0.0 | 0.0 | 82.7 | 24.8 | 347.3 | 104.2 |
| Eluate 5 | 300 | 12 | 25 | 5.0 | 12.4 | 0.4 | 343.3 | 103.0 | 0.0 | 0.0 | 46.9 | 14.1 | 192.4 | 57.7 |
| *Regeneration: 50% ethanol, 45° C., pH 12* |||||||||||||||
| Regen 1 | 600 | 24 | 25.0 | 5.0 | 12.5 | | 191.8 | 115.1 | 0.0 | 0.0 | 32.0 | 19.2 | 102.7 | 61.6 |
| *Regeneration: 10% Na citrate/water, both at 45° C.* |||||||||||||||
| Regen 2 | 600 | 24 | 25 | | 12.3 | | 19.0 | 11.4 | 0.0 | 0.0 | 7.9 | 4.7 | 10.0 | 6.0 |
| Regen 3 | 600 | 24 | 25 | | 11.3 | | 0.0 | 0.0 | 0.0 | 0.0 | 0.0 | 0.0 | 0.0 | 0.0 |

[see source document for table values; commas in numerical values denote decimal points.]

TABLE I.4

Column test for stability of column material
Elution after 14 days storage at 4° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) | | | | | | | | | | | | | | |
| Starting content: | 7700 | | | | | | 113.6 | 874.7 | 89.7 | 690.7 | 965.3 | 7432.8 | 66.8 | 514.4 |
| Washing: water with NaOH (2%), pH 13 | | | | | | | | | | | | | | |
| Wash 1 | 300 | 12 | 25 | 5.0 | 9.3 | | 77.3 | 23.2 | 42.6 | 12.8 | 1255.0 | 376.8 | 55.9 | 16.8 |
| Wash 2 | 300 | 12 | 25 | 5.0 | 13.1 | | 28.0 | 8.4 | 454.6 | 136.4 | 6000.0 | 1800.0 | 139.3 | 41.8 |
| Wash 3 | 300 | 12 | 25 | 5.0 | 13.1 | | 8.8 | 2.6 | 30.2 | 9.1 | 494.3 | 148.3 | 9.4 | 2.8 |
| Wash 4 | 300 | 12 | 25 | 5.0 | 13.1 | | 8.2 | 2.5 | 0.0 | 0.0 | 44.3 | 13.3 | 5.3 | 1.6 |
| Wash 5 | 300 | 12 | 25 | 5.0 | 13.2 | | 8.0 | 2.4 | 0.0 | 0.0 | 14.5 | 4.4 | 4.7 | 1.4 |
| Elution: Ethanol 30%, 45° C., pH 12 | | | | | | | | | | | | | | |
| Eluate 1 | 300 | 12 | 25 | 5.0 | 13.1 | 3.5 | 79.8 | 23.9 | 5.0 | 1.5 | 34.2 | 10.3 | 45.6 | 13.7 |
| Eluate 2 | 300 | 12 | 25 | 5.0 | 12.8 | 1.8 | 2528.0 | 758.4 | 0.0 | 0.0 | 0.0 | 0.0 | 1625.8 | 487.7 |
| Eluate 3 | 300 | 12 | 25 | 5.0 | 12.6 | 0.4 | 577.8 | 173.3 | 0.0 | 0.0 | 56.8 | 17.0 | 335.6 | 100.7 |
| Eluate 4 | 300 | 12 | 25 | 5.0 | 12.6 | 0.1 | 131.0 | 39.3 | 0.0 | 0.0 | 20.9 | 6.3 | 81.5 | 24.5 |
| Eluate 5 | 300 | 12 | 25 | 5.0 | 12.6 | 0.1 | 38.5 | 11.6 | 0.0 | 0.0 | 8.8 | 2.6 | 23.6 | 7.1 |
| Regeneration: 50% ethanol, 45° C., pH 12 | | | | | | | | | | | | | | |
| Regen 1 | 600 | 24 | 25.0 | 5.0 | 12.6 | | 21.2 | 12.7 | 0.0 | 0.0 | 9.6 | 5.8 | 12.1 | 7.3 |
| Regeneration: 10% Na citrate/water, both at 45° C. | | | | | | | | | | | | | | |
| Regen 2 | 600 | 24 | 25 | | 12.4 | | 4.0 | 2.4 | 0.0 | 0.0 | 2.4 | 1.4 | 2.3 | 1.4 |
| Regen 3 | 600 | 24 | 25 | | 11.4 | | 0.0 | 0.0 | 0.0 | 0.0 | 0.0 | 0.0 | 0.0 | 0.0 |

[see source document for table values; commas in numerical values denote decimal points.]

TABLE I.5

Column test for stability of column material
Elution after 14 days storage at 25° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) | | | | | | | | | | | | | | |
| Starting content: | 7700 | | | | | | 113.6 | 874.7 | 89.7 | 690.7 | 965.3 | 7432.8 | 66.8 | 514.4 |
| Washing: water with NaOH (2%), pH 13 | | | | | | | | | | | | | | |
| Wash 1 | 300 | 12 | 25 | 5.0 | 9.3 | | 25.9 | 7.8 | 502.5 | 150.8 | 6000.0 | 1800.0 | 130.0 | 39.0 |
| Wash 2 | 300 | 12 | 25 | 5.0 | 13.0 | | 65.5 | 19.7 | 130.1 | 39.0 | 2188.5 | 656.6 | 53.4 | 16.0 |
| Wash 3 | 300 | 12 | 25 | 5.0 | 13.1 | | 8.6 | 2.6 | 26.8 | 8.0 | 707.3 | 212.2 | 10.0 | 3.0 |
| Wash 4 | 300 | 12 | 25 | 5.0 | 13.1 | | 7.2 | 2.2 | 5.2 | 1.6 | 76.1 | 22.8 | 3.3 | 1.0 |
| Wash 5 | 300 | 12 | 25 | 5.0 | 13.1 | | 7.6 | 2.3 | 0.0 | 0.0 | 32.2 | 9.7 | 4.5 | 1.4 |
| Elution: Ethanol 30%, 45° C., pH 12 | | | | | | | | | | | | | | |
| Eluate 1 | 300 | 12 | 25 | 5.0 | 13.1 | 3.5 | 170.5 | 51.2 | 3.7 | 1.1 | 55.8 | 16.7 | 97.3 | 29.2 |
| Eluate 2 | 300 | 12 | 25 | 5.0 | 13.0 | 1.6 | 1586.2 | 475.0 | 3.7 | 1.1 | 0.0 | 0.0 | 927.0 | 278.1 |
| Eluate 3 | 300 | 12 | 25 | 5.0 | 12.5 | 0.6 | 807.0 | 242.1 | 0 | 0.0 | 0.0 | 0.0 | 499.3 | 149.8 |
| Eluate 4 | 300 | 12 | 25 | 5.0 | 12.5 | 0.3 | 325.4 | 97.6 | 1.2 | 0.4 | 41.8 | 12.5 | 214.0 | 64.2 |
| Eluate 5 | 300 | 12 | 25 | 5.0 | 12.4 | 0.2 | 175.9 | 52.8 | 0.5 | 0.2 | 22.7 | 6.8 | 106.6 | 32.0 |
| Regeneration: 50% ethanol, 45° C., pH 12 | | | | | | | | | | | | | | |
| Regen 1 | 600 | 24 | 25.0 | 5.0 | 12.4 | | 163.6 0.0 | 98.2 | 1.1 | 0.7 | 25.4 | 15.2 | 99.1 | 59.5 |
| Regen 2 | 600 | 24 | 25 | | 11.7 | | 24.5 | 14.7 | 0.0 | 0.0 | 6.9 | 4.1 | 14.7 | 8.8 |
| Regen 3 | 600 | 24 | 25 | | 10.0 | | 0.0 | 0.0 | 0.0 | 0.0 | 0.0 | 0.0 | 0.0 | 0.8 |

[see source document for table values; commas in numerical values denote decimal points.]

TABLE I.6

Column test for stability of column material
Elution after 35 days storage, 4° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) ||||||||||||||
| Starting content: | 7700 | | | | | | 113.6 | 874.7 | 89.7 | 690.7 | 965.3 | 7432.8 | 66.8 | 514.4 |
| Washing: water with NaOH (2%), pH 13 ||||||||||||||
| Wash 1 | 300 | 12 | 25 | 5.0 | 9.2 | | 89.6 | 26.9 | 76.4 | 22.9 | 1687.2 | 506.2 | 64.0 | 19.2 |
| Wash 2 | 300 | 12 | 25 | 5.0 | 13.0 | | 48.9 | 14.7 | 16.9 | 5.1 | 6157.1 | 1847.1 | 176.2 | 52.8 |
| Wash 3 | 300 | 12 | 25 | 5.0 | 13.1 | | 9.2 | 2.8 | 40.5 | 12.2 | 899.7 | 269.9 | 13.5 | 4.1 |
| Wash 4 | 300 | 12 | 25 | 5.0 | 13.1 | | 8.9 | 2.7 | 3.0 | 0.9 | 96.8 | 29.0 | 6.9 | 2.1 |
| Wash 5 | 300 | 12 | 25 | 5.0 | 13.0 | | 7.6 | 2.3 | 0.0 | 0.0 | 42.0 | 12.6 | 4.3 | 1.3 |
| Elution: Ethanol 30%, 45° C., pH 12 ||||||||||||||
| Eluate 1 | 300 | 12 | 25 | 5.0 | 13.0 | 3.6 | 73.3 | 22.0 | 5.4 | 1.6 | 62.1 | 18.6 | 38.9 | 11.7 |
| Eluate 2 | 300 | 12 | 25 | 5.0 | 12.7 | 2.0 | 2437.2 | 731.2 | 0.0 | 0.0 | 147.1 | 44.1 | 1386.8 | 416.9 |
| Eluate 3 | 300 | 12 | 25 | 5.0 | 12.3 | 0.5 | 769.5 | 230.0 | 0.0 | 0.0 | 69.0 | 20.7 | 438.8 | 131.6 |
| Eluate 4 | 300 | 12 | 25 | 5.0 | 12.6 | 0.3 | 223.5 | 67.1 | 1.3 | 0.4 | 52.6 | 15.8 | 126.6 | 38.0 |
| Eluate 5 | 300 | 12 | 25 | 5.0 | 12.5 | 0.1 | 66.7 | 20.0 | 0.0 | 0.0 | 20.6 | 6.2 | 39.8 | 11.9 |
| Regeneration: 50% ethanol, 45° C., pH 12 ||||||||||||||
| Regen 1 | 600 | 24 | 25.0 | 5.0 | 12.4 | | 15.5 | 9.3 | 0.0 | 0.0 | 14.3 | 8.6 | 15.3 | 9.2 |
| Regeneration: 10% Na citrate/water, both at 45° C. ||||||||||||||
| Regen 2 | 600 | 24 | 25 | | 12.0 | | 1.4 | 0.8 | 0.0 | 0.0 | 7.5 | 4.5 | 1.1 | 0.7 |
| Regen 3 | 600 | 24 | 25 | | 10.9 | | 0.0 | 0.0 | 0.0 | 0.0 | 0.8 | 0.5 | 0.0 | 0.0 |

[see source document for table values; commas in numerical values denote decimal points.]

TABLE I.7

Column test for stability of column material
Elution after 35 days storage, 25° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) ||||||||||||||
| Starting content: | 7700 | | | | | | 113.6 | 874.7 | 89.7 | 690.7 | 965.3 | 7432.8 | 66.8 | 514.4 |
| Washing: water with NaOH (2%), pH 13 ||||||||||||||
| Wash 1 | 300 | 12 | 25 | 5.0 | 9.2 | | 68.8 | 20.6 | 91.6 | 27.5 | 1595.4 | 478.6 | 34.5 | 10.4 |
| Wash 2 | 300 | 12 | 25 | 5.0 | 13.0 | | 46.6 | 14.0 | 17.0 | 5.1 | 6050.3 | 1815.1 | 151.6 | 45.5 |
| Wash 3 | 300 | 12 | 25 | 5.0 | 13.1 | | 8.8 | 2.6 | 3.6 | 1.1 | 1168.2 | 350.5 | 14.2 | 4.3 |
| Wash 4 | 300 | 12 | 25 | 5.0 | 13.1 | | 7.9 | 2.4 | 11.7 | 3.5 | 351.1 | 105.3 | 5.4 | 1.6 |
| Wash 5 | 300 | 12 | 25 | 5.0 | 13.1 | | 8.0 | 2.4 | 0.0 | 0.0 | 134.4 | 40.3 | 4.7 | 1.4 |
| Elution: Ethanol 30%, 45° C., pH 12 ||||||||||||||
| Eluate 1 | 300 | 12 | 25 | 5.0 | 13.0 | 3.5 | 118.4 | 35.5 | 7.5 | 2.3 | 101.2 | 30.4 | 64.8 | 19.4 |
| Eluate 2 | 300 | 12 | 25 | 5.0 | 12.9 | 1.6 | 1525.9 | 457.8 | 0.0 | 0.0 | 199.2 | 59.8 | 811.4 | 243.4 |
| Eluate 3 | 300 | 12 | 25 | 5.0 | 12.6 | 0.7 | 987.7 | 296.3 | 0.0 | 0.0 | 139.1 | 41.7 | 512.4 | 153.7 |
| Eluate 4 | 300 | 12 | 25 | 5.0 | 12.4 | 0.3 | 479.4 | 143.8 | 2.2 | 0.7 | 71.1 | 21.3 | 251.5 | 75.5 |
| Eluate 5 | 300 | 12 | 25 | 5.0 | 12.3 | 0.3 | 241.0 | 72.3 | 0.0 | 0.0 | 22.5 | 6.8 | 125.7 | 37.7 |
| Regeneration: 50% ethanol, 45° C., pH 12 ||||||||||||||
| Regen 1 | 600 | 24 | 25.0 | 5.0 | 12.3 | | 110.9 | 66.5 | 1.5 | 0.9 | 15.9 | 9.5 | 58.3 | 35.0 |
| Regeneration: 10% Na citrate/water, both at 45° C. ||||||||||||||
| Regen 2 | 600 | 24 | 25 | | 11.9 | | 9.6 | 5.8 | 0.0 | 0.0 | 6.7 | 4.0 | 5.6 | 3.4 |
| Regen 3 | 600 | 24 | 25 | | 10.0 | | 0.0 | 0.0 | 0.0 | 0.0 | 0.0 | 0.0 | 0.0 | 0.0 |

[see source document for table values; commas in numerical values denote decimal points.]

TABLE I.8

Column test for stability of column material
Elution after 56 days storage, 4° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) |||||||||||||||
| Starting content: | 7700 | | | | | | 113.6 | 874.7 | 89.7 | 690.7 | 965.3 | 7432.8 | 66.8 | 514.4 |
| Washing: water with NaOH (2%), pH 13 |||||||||||||||
| Wash 1 | 300 | 12 | 25 | 5.0 | 9.2 | | 85.8 | 25.7 | 44.5 | 13.4 | 1171.3 | 351.4 | 44.6 | 13.4 |
| Wash 2 | 300 | 12 | 25 | 5.0 | 13.0 | | 74.8 | 22.4 | 457.2 | 137.2 | 5000.0 | 1500.0 | 113.5 | 34.1 |
| Wash 3 | 300 | 12 | 25 | 5.0 | 13.1 | | 9.6 | 2.9 | 34.1 | 10.2 | 702.2 | 210.7 | 7.5 | 2.3 |
| Wash 4 | 300 | 12 | 25 | 5.0 | 13.2 | | 8.9 | 2.7 | 4.3 | 1.3 | 63.5 | 19.1 | 4.0 | 1.2 |
| Wash 5 | 300 | 12 | 25 | 5.0 | 13.1 | | 8.9 | 2.7 | 0.0 | 0.0 | 23.9 | 7.2 | 3.7 | 1.1 |
| Elution: Ethanol 30%, 45° C., pH 12 |||||||||||||||
| Eluate 1 | 300 | 12 | 25 | 5.0 | 13.1 | 3.8 | 53.1 | 15.9 | 3.3 | 1.0 | 41.7 | 12.5 | 27.6 | 8.3 |
| Eluate 2 | 300 | 12 | 25 | 5.0 | 12.8 | 2.0 | 2289.1 | 686.7 | 5.8 | 1.7 | 0.0 | 0.0 | 1288.2 | 386.5 |
| Eluate 3 | 300 | 12 | 25 | 5.0 | 12.4 | 0.5 | 869.4 | 260.8 | 0.0 | 0.0 | 0.0 | 0.0 | 475.9 | 142.8 |
| Eluate 4 | 300 | 12 | 25 | 5.0 | 12.3 | 0.2 | 228.2 | 68.5 | 2.4 | 0.7 | 0.0 | 0.0 | 122.0 | 36.6 |
| Eluate 5 | 300 | 12 | 25 | 5.0 | 12.3 | 0.1 | 83.4 | 25.0 | 0.0 | 0.0 | 0.0 | 0.0 | 45.2 | 13.6 |
| Regeneration: 50% ethanol, 45° C., pH 12 |||||||||||||||
| Regen 1 | 600 | 24 | 25.0 | 5.0 | 12.2 | | 42.4 | 25.4 | 3.0 | 1.8 | 0.0 | 0.0 | 22.9 | 13.7 |
| Regeneration: 10% Na citrate/water, both at 45° C. |||||||||||||||
| Regen 2 | 600 | 24 | 25 | | 11.8 | | 3.1 | 1.9 | 0.0 | 0.0 | 2.2 | 1.3 | 1.5 | 0.9 |
| Regen 3 | 600 | 24 | 25 | | 10.8 | | 1.1 | 0.7 | 0.9 | 0.5 | 0.2 | 0.1 | 0.7 | 0.4 |

[see source document for table values; commas in numerical values denote decimal points.]

TABLE I.9

Column test for stability of column materail
Elution after 56 days storage, 25° C.
Adsorber: XAD-7, volume: 300 ml
Starting solution: native urine from Poland, ultrafiltered

| Samples | Vol. mL | Time min | Flow mL/min | Flow BV/hr | pH | TS % | Estrone mg/L | Estrone mg | HPMF mg/L | HPMF mg | Cresol mg/L | Cresol mg | Equilin mg/L | Equilin mg |
|---|---|---|---|---|---|---|---|---|---|---|---|---|---|---|
| Starting solution: 90 L loaded on a 3-L column (Table I.1, resin divided into 10 portions of 300 mL each) |||||||||||||||
| Starting content: | 7700 | | | | | | 113.6 | 874.7 | 89.7 | 690.7 | 965.3 | 7432.8 | 66.8 | 514.4 |
| Washing: water with NaOH (2%), pH 13 |||||||||||||||
| Wash 1 | 300 | 12 | 25 | 5.0 | 9.2 | | 85.8 | 25.7 | 44.5 | 13.4 | 1171.3 | 351.4 | 44.6 | 13.4 |
| Wash 2 | 300 | 12 | 25 | 5.0 | 13.0 | | 74.8 | 22.4 | 457.2 | 137.2 | 5000.0 | 1500.0 | 113.5 | 34.1 |
| Wash 3 | 300 | 12 | 25 | 5.0 | 13.1 | | 9.6 | 2.9 | 34.1 | 10.2 | 702.2 | 210.7 | 7.5 | 2.3 |
| Wash 4 | 300 | 12 | 25 | 5.0 | 13.2 | | 8.9 | 2.7 | 4.3 | 1.3 | 63.5 | 19.1 | 4.0 | 1.2 |
| Wash 5 | 300 | 12 | 25 | 5.0 | 13.1 | | 8.9 | 2.7 | 0.0 | 0.0 | 23.9 | 7.2 | 3.7 | 1.1 |
| Elution: Ethanol 30%, 45° C., pH 12 |||||||||||||||
| Eluate 1 | 300 | 12 | 25 | 5.0 | 13.1 | 3.8 | 53.1 | 15.9 | 3.3 | 1.0 | 41.7 | 12.5 | 27.6 | 8.3 |
| Eluate 2 | 300 | 12 | 25 | 5.0 | 12.8 | 2.0 | 2289.1 | 686.7 | 5.8 | 1.7 | 0.0 | 0.0 | 1288.2 | 386.5 |
| Eluate 3 | 300 | 12 | 25 | 5.0 | 12.4 | 0.5 | 869.4 | 260.8 | 0.0 | 0.0 | 0.0 | 0.0 | 475.9 | 142.8 |
| Eluate 4 | 300 | 12 | 25 | 5.0 | 12.3 | 0.2 | 228.2 | 68.5 | 2.4 | 0.7 | 0.0 | 0.0 | 122.0 | 36.6 |
| Eluate 5 | 300 | 12 | 25 | 5.0 | 12.3 | 0.1 | 83.4 | 25.0 | 0.0 | 0.0 | 0.0 | 0.0 | 45.2 | 13.6 |
| Regeneration: 50% ethanol, 45° C., pH 12 |||||||||||||||
| Regen 1 | 600 | 24 | 25.0 | 5.0 | 12.2 | | 42.4 | 25.4 | 3.0 | 1.8 | 1.8 | 0.0 | 22.9 | 13.7 |
| Regeneration: 10% Na citrate/water, both at 45° C. |||||||||||||||
| Regen 2 | 600 | 24 | 25 | | 11.8 | | 3.1 | 1.9 | 0.0 | 0.0 | 2.2 | 1.3 | 1.5 | 0.9 |
| Regen 3 | 600 | 24 | 25 | | 10.8 | | 1.1 | 0.7 | 0.9 | 0.5 | 0.2 | 0.1 | 0.7 | 0.4 |

[see source document for table values; commas in numerical values denote decimal points.]

TABLE I.10

Summary of the results of the column stability tests

|  | Loading | Cartridge | Sample 1 | Sample 2 | Sample 3 | Sample 4 | Sample 5 | Sample 6 | Sample 7 | Sample 8 |
|---|---|---|---|---|---|---|---|---|---|---|
| Loading |  |  |  |  |  |  |  |  |  |  |
| Estrone (mg) | 10221 | 874.7 | 874.7 | 874.7 | 874.7 | 874.7 | 874.7 | 874.7 | 874.7 | 874.7 |
| Equilin (mg) | 6009 | 514.4 | 514.4 | 514.4 | 514.4 | 514.4 | 514.4 | 514.4 | 514.4 | 514.4 |
| Storage |  |  |  |  |  |  |  |  |  |  |
| Temperature | — | RT | 25 | 4 | 25 | 4 | 25 | 4 | 25 | 4 |
| Duration (days) | — | — | 7 | 7 | 14 | 14 | 35 | 35 | 56 | 56 |
| Washing |  |  |  |  |  |  |  |  |  |  |
| Estrone (mg) | — | 48.9 | 44.9 | 45.2 | 34.6 | 39.1 | 42 | 49.4 | 49.9 | 56.4 |
| Equilin (mg) | — | 44.3 | 39.5 | 34.4 | 60.4 | 64.4 | 63.2 | 69.6 | 44.5 | 52.1 |
| Elution |  |  |  |  |  |  |  |  |  |  |
| Estrone (mg) | Resin discharged, | 1014.1 | 897.1 | 926.8 | 919.6 | 1006.5 | 1005.7 | 1071.2 | 1087 | 1056.9 |
| Equilin (mg) | divided into 10 portions | 578.4 | 512.7 | 536.7 | 553.3 | 633.7 | 529.7 | 609.2 | 536.8 | 587.8 |
| Regeneration |  |  |  |  |  |  |  |  |  |  |
| Estrone (mg) |  | 26.0 | 126.6 | 114.3 | 112.9 | 15.1 | 72.3 | 10.1 | 10.2 | 28.0 |
| Equilin (mg) |  | 13.8 | 67.6 | 57.7 | 68.3 | 8.7 | 38.4 | 9.9 | 6.0 | 15.0 |
| Sum of Elution + Regeneration |  |  |  |  |  |  |  |  |  |  |
| Estrone |  | 1040.1 | 1023.6 | 1041.1 | 1032.5 | 1021.6 | 1078.0 | 1081.3 | 1097.2 | 1084.9 |
| Equilin |  | 592.2 | 580.3 | 594.4 | 5601.3 | 642.4 | 568.1 | 619.1 | 542.8 | 602.8 |

EXAMPLE 3

Stability Tests with Loaded Adsorption Columns for the Determination of Bacterial Counts The microbiological quality and harmlessness of natural starting materials for the production of pharmaceutical preparations have become increasingly important in recent times. Consequently, analyses were performed according to customary methods (pharmacopoeia) to determine bacterial counts in samples after storage of columns for five or eight weeks.

The results of the bacterial count determinations are presented in Table II. The total bacterial counts at a storage temperature of 4° C. were characterized as small. At a storage temperature of 25° C., the column wash water had 1.2 to 4.6*10$^6$ organisms, and the eluate had 80 to 170 organisms. However, it is noted that the stored column adsorbents were not washed or treated with preservative beforehand, and thus were initially subject to increased risk of bacterial growth. During storage without refrigeration, therefore, it is recommended that the loaded columns be thoroughly washed at least with water, and advantageously with additional stabilizing or preservative wash solutions such as sodium chloride solution.

TABLE II

Stability tests for bacterial count determination

|  | 5 Weeks Storage | | 8 Weeks Storage | |
|---|---|---|---|---|
|  | Storage time at ° C. | | | |
|  | 4° C. | 25° C. | 4° C. | 25° C. |
| Column wash water | 200 | 4.6 * 10$^6$ | 150 | 1.2 * 10$^6$ |
| Basic wash water | <1 | 18 | 3 | 14 |
| Ethanolic eluate | 20 | 80 | 3.5 | 170 |

*Data in CFU/ml (colony-forming units)

EXAMPLE 4

Stability Tests with Refrigerated, Loaded Adsorption Columns

As the result of seasonal or regional conditions, temperatures may fall below the freezing point during the storage or transport of loaded columns or cartridges, with the undesired result that the aqueous contents of the columns or cartridges solidify. Corresponding tests support the conclusion that the freezing process appears to have a negative influence on the elution of rethawed columns or cartridges. If the column cannot be wormed or maintained in a heated environment, or if storage takes place at low temperatures, it is recommended that the last wash be performed with suitable low-freezing mixtures instead of water to prevent freezing.

A) Test Procedure:

From the numerous possible low-freezing mixtures, of which several are given as illustrative examples in Table III.1, a sodium chloride solution, for example, was chosen for further tests. The addition of 23 g NaCl per 100 g water resulted in a freezing point of −21° C. The column loading proceeded in a conventional manner. After the urine was loaded, rinsing was performed with 3 bed volumes of water, followed by 2 bed volumes of a 33 wt-% NaCl solution. The column was then stored for 9 days in a chest freezer at −19° C.

TABLE III.1

Examples of liquid aqueous salt mixtures and low-freezing mixtures

| Achievable Temp. in ° C. | Substance A | g A/100 g coolant | Substance B |
|---|---|---|---|
| −3.4 | NH$_4$Cl | 23 | water |
| −5.3 | NaNO$_3$ | 43 | water |

TABLE III.1-continued

Examples of liquid aqueous salt mixtures and low-freezing mixtures

| Achievable Temp. in ° C. | Substance A | g A/100 g coolant | Substance B |
|---|---|---|---|
| −7.8 | $BaCl_2$ | 22 | ice |
| −10 | NaCl | 26 | water |
| −12 | $CaCl_2.6H_2O$ | 71 | water |
| −16 | $NH_4SCN$ | 57 | water |
| −19 | $(NH_4)_2SO_4$ | 38 | ice |
| −21 | NaCl | 23 | ice |
| −22 | $CaCl_2.6H_2O$ | 45 | ice |
| −28 | NaBr | 39 | ice |
| −33 | $MgCl_2$ | 22 | ice |
| −37 | 66.1% $H_2SO_4$ | 48 | snow |
| −40 | $CaCl_2.6H_2O$ | 55 | ice |
| −55 | $CaCl_2.6H_2O$ | 59 | ice |

B) Results

Even after 9 days of storage at −19° C., the contents of the column remained liquid, with no signs of partial solidification. Processing of the column, that is, basic washing, elution, and regeneration, proceeded normally. The total hormone content per total solids was approximately 22 wt-%. The results are shown in Table III.2.

Negative effects of the high NaCl content on the CE content and the separation of cresol and HPMF were not detectable. In summary, it may be concluded that stabilization of urine-loaded columns or cartridges using a liquid freezing mixture such as an aqueous sodium chloride solution, and storage under refrigeration, for example, down to approximately −20° C., have an advantageous effect, even for periods of 1.5 to 2 weeks. The contents of the columns or cartridges remained liquid, and processing of the columns or cartridges to isolate conjugated estrogens by washing, elution, and regeneration proceeded normally. Negative effects were not observed, even at high NaCl concentrations.

TABLE III.2

Column test for stability of column material
Elution after 9 days storage at −19.1° C.
Adsorber: XAD-7, volume: 200 mL

| Samples | Vol. mL | Time min | Flow mL/min | Flow BV/hr | pH | TS % | Cresol mg/L | Cresol mg | Equilin mg/L | Equilin mg | Estrone mg/L | Estrone mg | HPMF mg/L | HPMF mg | Estrone TS % |
|---|---|---|---|---|---|---|---|---|---|---|---|---|---|---|---|
| \multicolumn{16}{c}{Starting solution: 7 L loaded on a 3-L column = 35 bed volumes} |
| Run 1 | 1 | 62 | 16.1 | 4.8 | | | 61 | 61 | 0 | | 0 | | 0 | | |
| Run 2 | 1 | 61 | 16.4 | 4.9 | | | 96 | 96 | 0 | | 0 | | 0 | | |
| Run 3 | 1 | 62 | 16.1 | 4.8 | | | 111 | 111 | 0 | | 0 | | 0 | | |
| Run 4 | 1 | 61 | 16.4 | 4.9 | | | 111 | 111 | 0 | | 0 | | 6 | | |
| Run 5 | 1 | 61 | 16.4 | 4.9 | | | 275 | 275 | 0 | | 0 | | 28 | | |
| Run 6 | 1 | 61 | 16.4 | 4.9 | | | 267 | 267 | 0 | | 0 | | 27 | | |
| Run 7 | 1 | 61 | 16.4 | 4.9 | | | 392 | 392 | 0 | | 0 | | 32 | | |
| \multicolumn{16}{c}{Columns: water and 33% NaOH solution for storage at −19.1° C.} |
| w/water | 0.6 | 36 | 16.7 | 5.0 | | | 646 | 388 | 0 | | 0 | | 88 | | |
| w/salt solution | 0.4 | 25 | 16.0 | 4.8 | | | 465 | 186 | 0 | | 0 | | 5 | | |
| \multicolumn{16}{c}{Washing: water with NaOH (2%), pH 13} |
| Wash 1 | 0.2 | 12 | 16.7 | 5.0 | | | 70 | 14 | 0 | | 0 | | 0 | | |
| Wash 2 | 0.2 | 11 | 18.2 | 5.5 | | | 20038 | 4008 | 0 | | 70 | 14 | 348 | | |
| Wash 3 | 0.2 | 11 | 18.2 | 5.5 | | | 4009 | 802 | 32 | | 15 | 3 | 114 | | |
| Wash 4 | 0.2 | 11 | 18.2 | 5.5 | | | 287 | 57 | 10 | 2 | 0 | 0 | 31 | | |
| Wash 5 | 0.2 | 11 | 18.2 | 5.5 | | | 89 | 18 | 9 | 2 | 0 | 0 | 11 | | |
| \multicolumn{16}{c}{Elution: Ethanol 30%, 45° C., pH 12} |
| Eluate 1 | 0.2 | 12 | 16.7 | 5.0 | 12.1 | 4.1 | 81 | 16 | 13 | 3 | 8 | 2 | 5 | 25 | 0.02 |
| Eluate 2 | 0.2 | 12 | 16.7 | 5.0 | 13.3 | 2.5 | 266 | 53 | 1135 | 227 | 2036 | 407 | 0 | 0 | 8.14 |
| Eluate 3 | 0.2 | 11 | 18.2 | 5.5 | 12.6 | 0.5 | 114 | 23 | 493 | 99 | 854 | 171 | 0 | 0 | 17.08 |
| Eluate 4 | 0.2 | 11 | 18.2 | 5.5 | 12.4 | 0.1 | 62 | 12 | 32 | 6 | 85 | 17 | 4 | 22 | 8.50 |
| Eluate 5 | 0.2 | 12 | 16.7 | 5.0 | 12.4 | 0.1 | 24 | 5 | 8 | 2 | 17 | 3 | 2 | 10 | 1.70 |
| \multicolumn{16}{c}{Regeneration: 50% ethanol, 45° C., pH 12} |
| Regen 1 | 0.4 | 24 | 16.7 | 5.0 | | | 14.0 | | n.b. | | n.b. | | n.b. | | |
| \multicolumn{16}{c}{Regeneration: 10% Na citrate/water, both at 45° C.} |
| Regen 2 | 0.4 | 24 | 16.7 | 5.0 | | | 13.0 | | n.b. | | n.b. | | n.b. | | |
| Regen 3 | 0.4 | 24 | 16.7 | 5.0 | | | n.b. | | n.b. | | n.b. | | n.b. | | |

[see source document for table values; commas in numerical values denote decimal points.]

EXAMPLE 5

Concentration and Stabilization of Urine in a Field Test

A) General

The objective of a field test is to show that, with sufficient hormone content in the urine, satisfactory results can be obtained not only in the laboratory, but also under production conditions. A test was conducted under the same conditions that would occur during a sampling session at any given location.

B) Test Procedure

Fresh urine of sufficient quality was collected at a stud farm. With three horses that produced 15 to 20 liters of urine per day, a total of approximately 150 to 200 liters of urine was obtained in 10 days. Therefore, a 5 liter adsorption column was chosen for adsorption. Urine collection was started on a weekend, and the daily loading with urine, excluding weekends, was carried out according to the following program:

| | |
|---|---|
| Monday: | Charging of urine from Saturday, Sunday, and Monday |
| Tuesday through Friday: | Charging of urine from each day |
| Monday | Charging of urine from Saturday, Sunday, and Monday |
| Tuesday | Elution |

The urine was charged directly on the column at a loading rate of about 4.5 bed volumes per hour, with only a single cotton plug having a separation limit of 20 μm serving as a prefilter. In order to make the conditions more severe, no rinsing with water was performed between the individual charges. In pretests it was possible to deliver up to 450 liters of urine through the cotton plug with no pressure loss. In this field test, filtration proved to be difficult as a result of an unexpectedly high amount of calcium carbonate sediment and/or mucins.

After each 40 to 50 liters, a blockage appeared, along with a pressure rise of approximately 4 bar, which required the filter to be replaced. Depending on the calcium carbonate and/or mucin content, the optional addition of filtration aids is recommended.

Although the plug allowed sediment particles >20 μm in size to pass through, augmentation of the adsorption column was not indicated.

C) Results

Hormone Content

The results of this field test are presented in Table IV.

The estrone and equilin contents of 123 mg/liter and 74 mg/liter, respectively, in the raw urine were surprisingly high, corresponding to urine of average to good quality. However, the cresol values, at 531 mg/liter, were unexpectedly high in fresh urine, which hitherto had not been observed. The diet of the animals plays a role here and is a factor which should be considered. Although fundamentally, a high cresol content, for example, can be overcome, in individual cases it may be problematic. Therefore, it may be necessary to prolong the alkaline washing process during processing to minimize the cresol values in the ethanolic eluate. Otherwise, the adsorption and desorption proceeded normally. The eluate showed a pronounced content of estrone and equilin. Eluates 2 and 3 contained more than 95% estrone/equilin. The total hormone content relative to the total solids content was approximately 30 wt-%, thus meeting expectations for the test and achieving superior concentration to a hormone/total solids content greater than 15 wt-% under severe test conditions.

TABLE IV.1

Field test for stabilizing and concentrating CE
Test days: 1–10, column loading (on 7 working days)
Adsorber: XAD-7, volume: 5 Liters
Starting solution: native urine, untreated
The column was traversed from bottom to top.

| Samples | Vol. L | Time min | Flow mL/min | Flow BV/hr | pH | TS % | Estrone | Estrone mg | Cresol mg/L | Cresol mg | Equilin Mg/L | Equilin mg | HPMF mg/L | Estrone/ TS % |
|---|---|---|---|---|---|---|---|---|---|---|---|---|---|---|
| | | | | Starting solution: 140 L loaded on a 5-L column = 28 bed volumes (total quantity from 7 individual charges) | | | | | | | | | | |
| Starting content | 140 | | | | 9.0 | 6 | 112.5 | | 531.1 | | 37.4 | | 42.5 | |
| | | | | Loading: water with NaOH (2%), pH 13 | | | | | | | | | | |
| Run 1 | 10 | 26 | 384.6 | 4.6 | | | | 0 | 0.0 | 0 | 0 | | 0 | |
| Run 2 | 10 | 27 | 370.4 | 4.4 | | | | 0 | 249 | 2490 | 0 | | 0 | |
| Run 3 | 10 | 27 | 370.4 | 4.4 | | | | 0 | 245 | 2450 | 0 | | 0 | |
| Run 4 | 10 | 28 | 357.1 | 4.3 | | | | 0 | 408 | 4080 | 0 | | 0 | |
| Run 5 | 10 | 27 | 370.4 | 4.4 | | | | 0 | 358 | 3580 | 0 | | 0 | |
| Run 6 | 10 | 23 | 434.8 | 5.2 | | | | 0 | 537 | 5370 | 0 | | 0 | |
| Run 7 | 10 | 29 | 344.8 | 4.1 | | | | 0 | 901 | 9010 | 0 | | 0 | |
| Run 8 | 10 | 29 | 344.8 | 4.1 | 8.7 | | | 0 | 836 | 8360 | 0 | | 0 | |
| Run 9 | 10 | 29 | 344.8 | 4.1 | | | | 0 | 581 | 5810 | 0 | | 0 | |
| Run 10 | 10 | 24 | 416.7 | 5.0 | | | | 0 | 605 | 6050 | 0 | | 0 | |
| Run 11 | 10 | 25 | 400.0 | 4.8 | | | | 0 | 621 | 6210 | 0 | | 0 | |
| Run 12 | 10 | 27 | 370.4 | 4.4 | | | | 0 | 509 | 5090 | 0 | | 0 | |
| Run 13 | 10 | 27 | 370.4 | 4.4 | | | | 0 | 668 | 6680 | 0 | | 0 | |
| Run 14 | 10 | 24 | 416.7 | 5.0 | | | | 0 | 655 | 6550 | 0 | | 0 | |

[see source document for table values; commas in numerical values denote decimal points.]

TABLE IV.2

Field test for stabilizing and concentrating CE
Processing of column on Test Day 11
Adsorber: XAD-7, volume: 5 Liters
Starting solution: native urine, untreated
The column was traversed from bottom to top.

| Samples | Vol. L | Time min | Flow mL/min | Flow BV/hr | pH | TS % | Estrone mg/L | Estrone mg | Cresol mg/L | Cresol mg | Equilin mg/L | Equilin mg | HPMF mg/L | Estrone/ TS % |
|---|---|---|---|---|---|---|---|---|---|---|---|---|---|---|
| Starting content | 140 | | | | 9.0 | 6 | 112.5 | | 531.1 | | 37.4 | | 42.5 | |
| Washing: water with NaOH (2%), pH 13 ||||||||||||||
| Wash 1 | 5 | 15 | 333.3 | 4.0 | | | 0 | | 1104 | 5520 | 0 | | 40 | |
| Wash 2 | 5 | 15 | 333.3 | 4.0 | | | 0 | | 4400 | 22000 | 0 | | 252 | |
| Wash 3 | 5 | 14 | 357.1 | 4.3 | | | 0 | | 2355 | 11775 | 0 | | 60 | |
| Wash 4 | 5 | 14 | 357.1 | 4.3 | | | 0 | | 40 | 200 | 0 | | 0 | |
| Wash 5 | 5 | 14 | 357.1 | 4.3 | | | 0 | | 7 | 35 | 0 | | 0 | |
| Elution: Ethanol 30%, 45° C., pH 12 ||||||||||||||
| Eluate 1 | 5 | 8 | 625.0 | 7.5 | | 3.8 | 23 | 115 | 12 | 60 | 9 | 45 | 0 | 0.1 |
| Eluate 2 | 5 | 10 | 500.0 | 6.0 | | 2.0 | 2797 | 13985 | 201 | 1005 | 1211 | 6055 | 0 | 14.0 |
| Eluate 3 | 5 | 12 | 416.7 | 5.0 | | 0.3 | 481 | 2405 | 0 | 0 | 193 | 965 | 0 | 16.0 |
| Eluate 4 | 5 | 13 | 384.6 | 4.6 | | 0.0 | 14 | 70 | 0 | 0 | 7 | 35 | 0 | |
| Eluate 5 | 5 | 13 | 384.6 | 4.6 | | 0.0 | 0 | 0 | 0 | 0 | 0 | 0 | 0 | |
| Regeneration: 50% ethanol, 45° C., pH 12 ||||||||||||||
| Regen 1 | 10 | 0.4 | 0.4 | 0.0 | 1 | | 0 | | 0 | | 0 | | 0 | |
| Regeneration: 10% Na citrate/water, both at 45° C. ||||||||||||||
| Regen 2 | 10 | 0.4 | 0.4 | 0.0 | 11.3 | | 0 | | 0 | | 0 | | 0 | |
| Regen 3 | 10 | 0.4 | 0.4 | 0.0 | 10.3 | | 0 | | 0 | | 0 | | 0 | |
| Regen. 4 | 2 BV water rinsed from bottom to top |||||||||||||

[see source document for table values; commas in numerical values denote decimal points.]

Bacterial Counts

In addition to urine adsorption, possible growth of bacteria on the column was investigated. Under the following conditions,
1. Charging of contaminated raw urine (the cotton plug filter did not separate any bacteria),
2. No rinsing after daily charging,
3. Test carried out a room temperature, and
4. Test duration of 10 days, the bacterial density on the column and subsequent growth thereon were not precluded. Determination of the total bacterial count at different adsorption steps gave the following results:

| Sample | Total bacterial count/ml |
|---|---|
| Raw urine | $1.1 * 10^8$ |
| Column wash water after 10 days | $1.1 * 10^8$ |
| Basic wash water | <1 |
| Main eluate | 1.5 |

D) Summary of Results

Fresh urine was charged on a 5 liter adsorption column over a test period of 10 days. The entire volume of urine was 140 liters, with an average estrone and equilin content of 123 mg/liter and 74 mg/liter, respectively.

Column rinsing with water after the daily urine adsorption was intentionally omitted. Both of the very pronounced main eluates contained approximately 93% estrone and equilin. The total hormone content relative to total solids was approximately 30 wt-%. A further surprising result related to possible bacterial contamination of the column. In spite of charging highly contaminated raw urine, bacterial growth on the column itself was not detectable after 10 days. With 1.5 organisms/ml, the eluate obtained was practically bacteria-free. Hence, under severe conditions it was proven on a large scale which, with sufficient hormone in the raw urine, stabilization and concentration to a hormone/total solids content of greater than 15% and of good quality can be performed using an adsorption column.

EXAMPLE 6

Filtration Tests Using Filter Cartridges

Filtration tests using filter cartridges were carried out in a further field test, the results of which are summarized below.

Related Material: Fresh Urine from a German Stud Farm.

The urine of pregnant mares which had been collected in drums and occasionally agitated was pumped from the drums using a hose pump, through a 5μ bag (prefilter), and into a container. Sediment of about 0.5 wt-% remained in the container. FIG. 2 shows a schematic representation of the method for filtering raw urine.

1st Test:

| Bag | 5μ |
|---|---|
| Filter cartridges | 5μ, 3μ, 1μ connected in series |
| Membrane filter | 2 × 1.2μ connected in parallel |
| Column loading | 95 liters of filtrate |
| Sediment filtrate | 0.000% |

2nd Test:

| Bag | 5μ |
|---|---|
| Filter cartridges | 5μ, 3μ, 1μ connected in series |
| Membrane filter | 2 × 3μ connected in parallel |
| Column loading | 142 liters of filtrate |
| Sediment filtrate | 0.001% |

3rd Test:

| Bag | 5μ |
|---|---|
| Filter cartridges | 3μ, 1μ connected in series |
| Membrane filter | 2 × 1μ connected in parallel |
| Column loading | 160 liters filtrate |
| Sediment filtrate | 0.000% |

In each test, one sample was taken downstream of the membrane filter. After every 100 liters a sample was taken from the outlet, downstream of the column. The total column loading was 397 liters of filtrate. The total solids (TS) content after processing was 5.9 wt-%.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

The invention claimed is:

1. A method for concentrating and stabilizing mixtures of conjugated estrogens from pregnant mare urine in a decentralized manner that can be carried out in the field, comprising
   pumping a predetermined maximum total amount of collected liquid pregnant mare urine from a supply vessel at a predetermined flow rate through an upright cartridge containing a solid adsorbent support capable of adsorbing a predetermined quantity of conjugated estrogens such that the adsorbent is surrounded by a flow of the pumped liquid urine,
   whereby a natural mixture of conjugated estrogens from the urine is concentrated and stabilized by adsorption an said support;
   wherein the maximum total amount of liquid urine pumped through the cartridge is matched to the maximum loading capacity of the adsorbent for conjugated estrogens contained in the liquid urine, and pumping of the liquid urine through the cartridge is ceased at or before maximum loading of the adsorbent with conjugated estrogens is achieved;
   discarding liquid urine effluent depleted in conjugated estrogens from the cartridge,
   wherein the cartridge is not rinsed with a preservative solution containing a preservative agent after loading of the adsorbent with conjugated estrogens;
   storing said upright cartridge containing the solid adsorbent support with the concentrated and stabilized natural mixture of conjugated estrogens adsorbed thereon, and
   transporting said upright cartridge containing the solid adsorbent support with the concentrated and stabilized natural mixture of conjugated estrogens from the urine to a processing site, where the conjugated estrogens are eluted from the adsorbent
   wherein the adsorbent is a semipolar polymeric adsorber resin.

2. A method according to claim 1, wherein the preservative agent is selected from customary preservatives, germicides, bactericides and antihelmintic agents.

3. A method according to claim 1 wherein the liquid urine has been previously pre-purified by coarse mechanical filtration.

4. A method according to claim 1 wherein the urine is pumped continuously through said cartridge.

5. A method according to claim 1 wherein the urine is pumped through said cartridge in discrete portions.

6. A method according to claim 5 wherein the discrete portions of urine are pumped through said upright cartridge over a time period of several days partially or completely overlapping with the storage time period.

7. A method according to claim 1 wherein said cartridge has internal dimensions such that the cartridge can accommodate from 30 to 50 liters of adsorbent, and the pregnant mare urine is required to travel a path distance of 80 to 120 cm through the cartridge.

8. A method according to claim 1 wherein the cartridge is made of impact-resistant laboratory glass, plastic, or metal.

9. A method according to claim 1 wherein the liquid urine is pumped by a monopump, a hose pump, or membrane pump.

10. A method according to claim 1, wherein the flow rate is measured by flow meter selected from the group consisting of rotameter with a float, a vane air flow meter, or an inductive flow meter.

11. A method according to claim 1 wherein the quantity of liquid urine pumped through the cartridge is measured by a throughput meter.

12. A method according to claim 11 wherein said throughput meter is a water meter or an inductive throughput meter.

13. A method according to claim 1 wherein the urine flow has a flow velocity ranging from 3 to 10 adsorber bed volumes per hour.

14. A method according to claim 13 wherein the urine flow velocity ranges from 4 to 6 adsorber bed volumes per hour.

15. A method according to claim 1 wherein the semipolar polymeric adsorber resin has an intermediate polarity having a dipole moment of the active resin surface in a range of 1.0 to 3.0 Debye.

16. A method according to claim 1 wherein the semi-polar polymeric adsorber resin is a macroporous polycarbaxylic acid ester resin.

17. A method according to claim 16 wherein the macroporous polycarboxylic acid ester resin is a cross-linked aliphatic polycarboxylic acid ester resin.

18. A method according to claim 17 wherein the cross-linked aliphatic polycarboxylic acid ester resin has a macroreticular structure.

19. A method according to claim 17 wherein the cross-linked aliphatic polycarboxylic acid ester resin is a cross-linked polyacrylic ester resin.

20. A method according to claim 1 wherein a maximum total quantity of liquid urine of from 20 to 60 adsorber bed volumes is passed through said cartridge.

21. A method according to claim 20 wherein the maximum total quantity of liquid urine is 30 to 40 adsorber bed volumes.

22. A method according to claim 1 wherein after loading of the adsorbent with a quantity of pregnant mare urine, the cartridge is rinsed with an aqueous wash solution.

23. A method according to claim 22 wherein the aqueous wash solution is a basic wash solution.

24. A method according to claim 23 wherein the basic wash solution is a 1 diluted aqueous sodium hydroxide solution.

25. A method according to claim 24 wherein the diluted aqueous sodium hydroxide solution is an aqueous 0.5-2N sodium hydroxide solution.

26. A method according to claim 22 wherein the rinsing is carried out after the adsorbent has been loaded with a quantity of pregnant mare urine containing an amount of conjugated estrogens corresponding approximately to the total capacity of the adsorbent to adsorb conjugated estrogens.

27. A method according to claim 22 wherein the cartridge is rinsed with water.

28. A method according to claim 22 wherein after loading of the adsorbent with a quantity of pregnant mare urine, the cartridge is rinsed with an aqueous wash solution, and thereafter further stabilized by rinsing with a pH-adjusted aqueous solution or an aqueous salt solution.

29. A method according to claim 28 wherein the cartridge is stabilized by rinsing with an aqueous salt solution.

30. A method according to claim 29 wherein the aqueous salt solution is a sodium chloride solution having a salt concentration of approximately 10 to 35 wt-%.

31. A method according to claim 29 wherein the aqueous salt solution is a sodium chloride solution having a salt concentration of approximately 25 to 33 wt-%.

32. A method according to claim 1 further comprising pumping the liquid urine from the supply vessel through at least one prefilter before the liquid urine is pumped through the cartridge.

33. A method according to claim 32 wherein said at least one prefilter comprises a deep-bed filter or a precoated filter.

34. A method according to claim 32 wherein said at least one prefilter comprises a deep-bed filter having a sand bed, a filter cartridge, a plate filter, a cartridge filter, a filter bag, or a filtration tube.

35. A method according to claim 32 wherein a filtering aid is added to the liquid urine before filtration.

36. A method according to claim 1 wherein the step of storing the upright cartridge containing the solid adsorbent support with the concentrated and stabilized natural mixture of conjugated estrogens adsorbed thereon lasts for at least several days.

37. A method according to claim 36 wherein the step of storing lasts far at least one week.

38. A method according to claim 36 wherein the step of storing lasts from several days to several weeks.

39. A method according to claim 36 wherein the step of storing lasts from several days to eight weeks.

40. A method according to claim 36 wherein the step of storing lasts from one week to eight weeks.

41. A method according to claim 1 further comprising the step of processing said upright cartridge with a solid adsorbent support containing concentrated and stabilized pregnant mare urine.

42. A method according to claim 1 wherein the step of pumping a predetermined maximum total amount of collected liquid pregnant mare urine from a supply vessel through an upright cartridge containing a solid adsorbent support capable of adsorbing a predetermined quantity of conjugated estrogens takes place at or near a collection site of pregnant mare urine.

43. A method according to claim 1 wherein the processing site is remote from the collection site.

* * * * *